(12) United States Patent
Griffith et al.

(10) Patent No.: US 10,906,929 B2
(45) Date of Patent: Feb. 2, 2021

(54) PHOSPHORAMIDATE NUCLEOSIDE DERIVATIVES AS ANTICANCER AGENTS

(71) Applicant: NuCana plc, Edinburgh (GB)

(72) Inventors: Hugh Griffith, Edinburgh (GB); Michaela Serpi, Cardiff (GB); Magdalena Slusarczyk, Cardiff (GB); Christopher McGuigan, Cardiff (GB)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 16/305,153

(22) PCT Filed: May 31, 2017

(86) PCT No.: PCT/GB2017/051549
§ 371 (c)(1),
(2) Date: Nov. 28, 2018

(87) PCT Pub. No.: WO2017/207986
PCT Pub. Date: Dec. 7, 2017

(65) Prior Publication Data
US 2019/0375779 A1   Dec. 12, 2019

(30) Foreign Application Priority Data

Jun. 1, 2016  (GB) .................................. 1609601.8

(51) Int. Cl.
C07H 19/207 (2006.01)
C07H 19/173 (2006.01)

(52) U.S. Cl.
CPC ......... *C07H 19/207* (2013.01); *C07H 19/173* (2013.01)

(58) Field of Classification Search
CPC ............................ C07H 19/173; C07H 19/207
See application file for complete search history.

(56) References Cited

U.S. PATENT DOCUMENTS

| | | | | |
|---|---|---|---|---|
| 8,263,575 B2* | 9/2012 | McGuigan | ............ | A61P 35/02 514/47 |
| 8,759,318 B2* | 6/2014 | Chamberlain | ....... | C07H 19/167 514/48 |
| 8,933,053 B2* | 1/2015 | McGuigan | ............ | C07H 19/10 514/51 |
| 9,156,874 B2* | 10/2015 | Chang | ................. | C07F 9/65616 |
| 9,221,866 B2* | 12/2015 | McGuigan | ............ | A61P 35/02 |
| 9,655,915 B2* | 5/2017 | McGuigan | ............ | A61K 45/06 |
| 10,022,390 B2* | 7/2018 | McGuigan | ............ | A61P 35/00 |
| 10,117,888 B2* | 11/2018 | Griffith | ................. | A61K 47/44 |
| 10,786,523 B2* | 9/2020 | Griffith | ................. | A61K 47/16 |
| 2009/0215715 A1 | 8/2009 | McGuigan et al. | | |
| 2012/0052046 A1 | 3/2012 | Chamberlain et al. | | |
| 2013/0210757 A1 | 8/2013 | Huang et al. | | |
| 2014/0057866 A1 | 2/2014 | McGuigan et al. | | |
| 2017/0095498 A1 | 4/2017 | Griffith et al. | | |
| 2019/0022118 A1 | 1/2019 | Griffith et al. | | |
| 2019/0374564 A1* | 12/2019 | Griffith | ................. | A61P 35/02 |
| 2019/0375779 A1 | 12/2019 | Griffith | | |

FOREIGN PATENT DOCUMENTS

| | | |
|---|---|---|
| WO | WO-2006/063149 A1 | 6/2006 |
| WO | WO-2006/100439 A1 | 9/2006 |
| WO | WO-2012/040126 A1 | 3/2012 |
| WO | WO-2012/117246 A1 | 9/2012 |
| WO | WO-2015/038596 A1 | 3/2015 |
| WO | WO-2015/081133 A2 | 6/2015 |
| WO | WO-2015/181624 A2 | 12/2015 |
| WO | WO-2015/198059 A1 | 12/2015 |

(Continued)

OTHER PUBLICATIONS

International Search Report for International Application No. PCT/GB2017/051549 dated Jul. 24, 2017.

Vande Voorde et al., "The cytostatic activity of NUC-3073, a phosphoramidate prodrug of 5-fluoro-2'-deoxyuridine, is independent of activation by thymidine kinase and insensitive to degradation by phosphorolytic enzymes," Biochemical Pharmacology, 82(5):441-452 (2011).

Birkus et a.l, "Cathepsin A Is the Major Hydrolase Catalyzing the Intracellular Hydrolysis of the Antiretroviral Nucleotide Phosphonoamidate Prodrugs GS-7340 and GS-9131," Antimicrobial Agents Chemotherapy, 51(2): 543-550 (2004).

Bronckaers et al., "The cytostatic activity of pyrimidine nucleosides is strongly modulated by Mycoplasma hyorhinis infection: Implications for cancer therapy," Biochemical Pharmacology, 76(2): 188-97 (2008).

Cahard et al., "Aryloxy Phosphoramidate Triesters as Pro-Tides," Mini Reviews in Medicinal Chemistry, 4(4): 371-381 (2004).

(Continued)

*Primary Examiner* — Lawrence E Crane
(74) *Attorney, Agent, or Firm* — Dana M. Gordon; Foley Hoag LLP

(57) ABSTRACT

This invention relates to derivatives of cladribine of Formula (I). The compounds are phosphoramidate derivatives in which the phosphoramidate moiety is situated on the 3'-hydroxyl group of cladribine. The invention also relates to pharmaceutical formulations of the cladribine derivatives and their use in methods of treatment. The compounds are useful in the treatment of cancer.

(I)

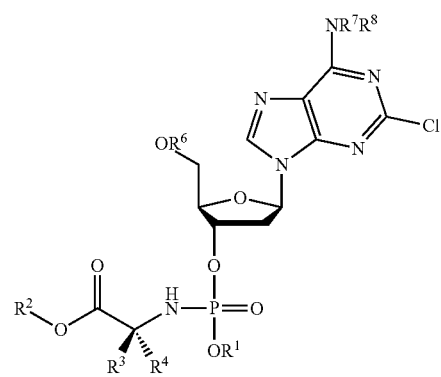

16 Claims, No Drawings

(56) References Cited

FOREIGN PATENT DOCUMENTS

| WO | WO-2016/083830 A1 | 6/2016 |
|---|---|---|
| WO | WO-2016/200851 A1 | 12/2016 |
| WO | WO-2017/207993 A1 | 12/2017 |

OTHER PUBLICATIONS

Chan et al., "Prevalence of mycoplasma conserved DNA in malignant ovarian cancer detected using sensitive PCR-ELISA," Gynecologic Oncology, 63(2): 258-260 (1996).

Charron et al., "Analysis of Deoxycytidine (dC) Deaminase Activity in Herpes Simplex Virus-infected or HSV TK-transformed Cells: Association with Mycoplasma Contamination but Not with Virus Infection," Journal of General Virology, 57: 245-50 (1981).

Derudas et al., "The Application of Phosphoramidate Protide Technology to Acyclovir Confers Anti-HIV Inhibition," Journal of Medicinal Chemistry, 52(17): 5520-553 (2009).

Galmarini et al., "Nucleoside analogues and nucleobases in cancer treatment," The Lancet Oncology, 3(7): 415-424 (2002).

Grem et al., "5-Fluorouracil: Forty-Plus and Still Ticking. A Review of its Preclinical and Clinical Development," Investigational New Drugs, 18: 299-313 (2000).

Griffith et al., "Enhanced Inhibition of the EDHF Phenomenon by a Phenyl Methoxyalaninyl Phosphoramidate Derivative of Dideoxyadenosine," British Journal of Pharmacology, 142(1): 27-30 (2004).

Huang et al., "Mycoplasma infections and different human carcinomas," World Journal of Gastroenterology, 7(2): 266-269 (2001).

Jette et al., "Resistance of colorectal cancer cells to 5-FUdR and 5-FU caused by Mycoplasma infection," Anticancer Research, 28: 2175-2180 (2008).

Jones et al., "Synthesis and anti-HIV activity of some novel phosphorodiamidate derivatives of 3'-asido-3'<deoxvthvmidine (AZT)," Antiviral Chemistry & Chemotherapy, 2(1): 35-39 (1991).

Kidder et al., "Assessment of archived paraffin-embedded cervical condyloma tissues for mycoplasma-conserved DNA using sensitive PCR-ELISA," Gynecol Oncology, 71(2): 254-257 (1998).

Lee et al., "Selective Intracellular Activation of a Novel Prodrug of the Human Immunodeficiency Virus Reverse Transcriptase Inhibitor Tenofovir Leads to Preferential Distribution and Accumulation in Lymphatic Tissue," Antimicrobial Agents and Chemotherapy, 49: 1898-1906 (2005).

Liekens et al., "Improvement of purine and pyrimidine antimetabolite-based anticancer treatment by selective suppression of mycoplasma-encoded catabolic enzymes," The Lancet Oncology, 10(6): 628-635 (2009).

McGuigan et al., "Anti-cancer ProTides: tuning the activity of BVDU phosphoramidates related to thymectacin," Bioorganic & Medicinal Chemistry, 13: 3219-3227 (2005).

McGuigan et al., "Application of Phosphoramidate Pronucleotide Technology to Abacavir Leads to a Significant Enhancement of Antiviral Potency," Journal of Medinical Chemistry, 48: 3504-3515 (2005).

McGuigan et al., "Design, synthesis and evaluation of a novel double pro-drug: INX-08189. A new clinical candidate for hepatitis C virus," Bioorganic & Medicinal Chemistry Letters, 20: 4850-4854 (2010).

McGuigan et al., "Phosphoramidate ProTides of the Anticancer Agent FUDR Successfully Deliver the Preformed Bioactive Monophosphate in Cells and Confer Advantage over the Parent Nucleoside," Journal of Medicinal Chemistry, 54(20): 7247-7258 (2011).

Mehellou et al., "Aryloxy phosphoramidate triesters: a technology for delivering mono-phosphorylated nucleosides and sugars into cells," Chem Med Chem 4(11):1779-1791 (2009).

Mehellou et al., "Phosphoramidates of 2'-B-d-arabinouridine (AraU) as phosphate prodrugs: design, synthesis, in vitro activity and metabolism," Bioorganic & Medicinal Chemistry, 18(7): 2439-2446 (2010).

Neale et al., "Enzymes of pyrimidine deoxyribonucleotide metabolism in *Mycoplasmamycoides* subsp. *mycoides*.," Journal of Bacteriology, 156: 1001-1005 (1983).

Pehlivan et al., "Can Mycoplasma-mediated oncogenesis be responsible for formation of conventional renal cell carcinoma?" Urology, 65(2): 411-414 (2005).
Pehlivan et al., "Does *Mycoplasma* sp. play role in small cell lung cancer?" Lung Cancer, 45(1): 129-130 (2004).
Razin et al., "Molecular biology and pathogenicity of Mycoplasmas," Microbiology and Molecular Biology Reviews, 62(4): 1094-1156 (1998).
Razin., "The mycoplasmas." Microbiology Reviews, 42(2): 414-70 (1978).
Robak., "New nucleoside analogs for patients with hematological malignancies," Expert Opinon on Investigational Drugs, 20(3): 343-359 (2011).
Sinigaglia et al., "Inhibition of [3H] thymidine incorporation by Mycoplasma arginini-infected cells due to enzymatic cleavage of the nucleoside," European Journal of Immunology, 15(7): 692-696 (1985).
Tham et al., "Identification of Mycoplasma pirum genes involved in the salvage pathways for nucleosides," Journal of Bacteriology, 175: 5281-5285 (1993).
Wagner et al., "Pronucleotides: Toward the In Vivo Delivery of Antiviral and Anticancer Nucleotides," Medicinal Research Reviews, 20(6): 417-451 (2000).
Yang et al., "Mycoplasma hyorhinis infection in gastric carcinoma and its effects on the malignant phenotypes of gastric cancer cells," BMC Gastroenterology, 10: Article 132 (2010).
Zhang et al., "Design, synthesis and anti-influenza virus activities of terminal modified antisense oligonucleotides," Tetrahedron Letters, 55 (1): 94-97 (2014).

* cited by examiner

PHOSPHORAMIDATE NUCLEOSIDE DERIVATIVES AS ANTICANCER AGENTS

RELATED APPLICATIONS

This application is a § 371 national stage application based on Patent Cooperation Treaty Application serial number PCT/GB2017/051549, filed May 31, 2017; which claims the benefit of priority to United Kingdom Patent Application No. GB 1609601.8, filed Jun. 1, 2016.

This invention relates to derivatives of cladribine. The compounds are phosphoramidate derivatives in which the phosphoramidate moiety is situated on the 3'-hydroxyl group of cladribine. The invention also relates to pharmaceutical formulations of the cladribine derivatives and their use in methods of treatment. The compounds are useful in the treatment of cancer.

BACKGROUND

Some modified purine nucleosides are known to display potent biological properties, including chemotherapeutic potential. An example is cladribine 1, a useful, but toxic drug. It is given by infusion for the treatment of leukaemia, and hairy cell leukaemia in particular. It is also used for chronic lymphocytic leukaemia in patients who have failed standard regimens with alkylating agents.

As with all nucleoside analogues, these agents require intracellular kinase-mediated activation to their bio-active 5'-phosphate forms.

WO2006100439 describes some phosphoramidate derivatives of cladribine and their anticancer activities. The phosphoramidates described in WO2006100439 are positioned on the 5'-hydroxyl group of cladribine, for example compound Y, and the phosphoramidate moiety acts as a prodrug for the nucleoside monophosphate.

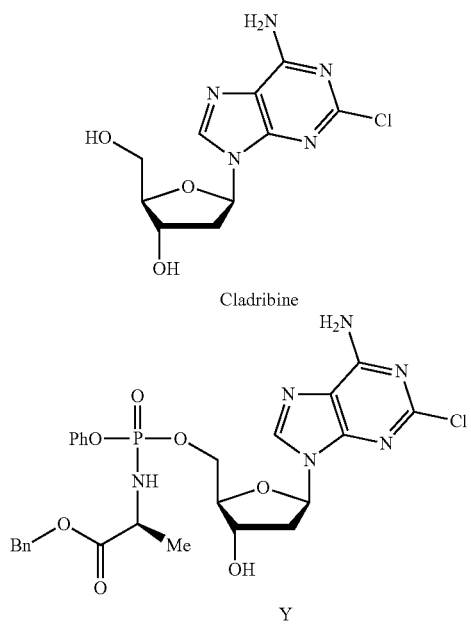

Phosphoramidates such as compound Y are known as ProTides. ProTides can offer significant benefits in terms of increasing the anticancer properties of nucleosides either by increasing potency or by avoiding both inherent and acquired resistance mechanisms ('*Application of Pro Tide Technology to Gemcitabine: A Successful Approach to Overcome the Key Cancer Resistance Mechanisms Leads to a New Agent (NUC-1031) in Clinical Development*'; Slusarczyk et al; *J. Med. Chem.*; 2014, 57, 1531-1542; *Phosphoramidate ProTides of the anticancer agent FUDR successfully deliver the preformed bioactive monophosphate in cells and confer advantage over the parent nucleoside; J. Med. Chem.*; 2011, 54, 7247-7258; and Vande Voorde et al.; *The cytostatic activity of NUC-3073, a phosphoramidate prodrug of 5-fluoro-2'-deoxyuridine, is independent of activation by thymidine kinase and insensitive to degradation by phosphorolytic enzymes; Biochem. Pharmacol.*; 2011, 82, 441-452).

However, while 5'-phosphoramidates have shown excellent anticancer activity, this is not typically the case with 3'-phosphoramidates which generally show only poor anticancer activity.

It is an aim of certain embodiments of this invention to provide new anticancer compounds. It is an aim of certain embodiments of this invention to provide compounds that are more effective anticancer compounds than prior art compounds.

It is an aim of certain embodiments of this invention to provide new compounds that target cancer stem cells. It is an aim of certain embodiments of this invention to provide compounds that are more effective at targeting cancer stem cells than prior art compounds.

It is an aim of certain embodiments of this invention to provide compounds that are less affected by mycoplasma infection than prior art compounds.

It is an aim of certain embodiments of this invention to provide compounds that are less affected by cancer resistance mechanisms than prior art compounds.

Certain embodiments of the invention achieve some or all of the above mentioned aims.

BRIEF SUMMARY OF THE DISCLOSURE

In accordance with the present inventions there is provided a compound of formula (I) or a pharmaceutically acceptable salt thereof:

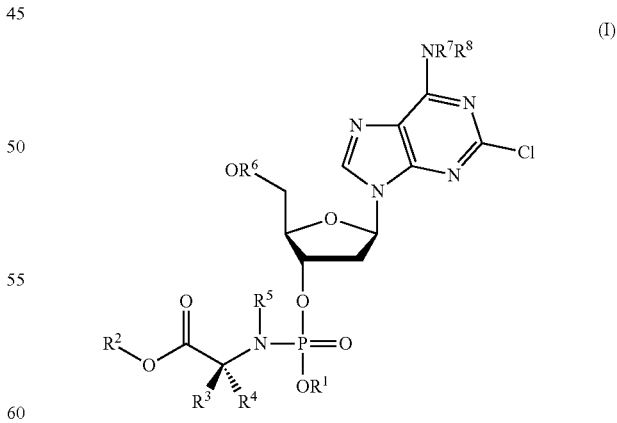

$R^1$ is aryl;
$R^2$ is selected from $C_1$-$C_{24}$-alkyl, $C_3$-$C_{24}$-alkenyl, $C_3$-$C_{24}$-alkynyl, $C_0$-$C_4$-alkylene-$C_3$-$C_7$-cycloalkyl or $C_0$-$C_4$-alkylene-aryl;
$R^3$ and $R^4$ are each independently selected from H, $C_1$-$C_6$-alkyl and $C_1$-$C_3$-alkylene-$R^9$; or wherein $R^3$ and $R^4$ together with the atom to which they are attached form a 3- to 6-membered cycloalkyl or heterocycloalkyl group;

$R^5$ and $R^7$ are each independently selected from H and $C_1$-$C_4$-alkyl;

$R^6$ is independently selected from H and $C(O)R^{10}$;

$R^8$ is independently selected from H, $C(O)OR^{19}$ and $C(O)R^{10}$;

$R^9$ is independently selected from aryl (e.g. phenyl), imidazole, indole, $SR^a$, $OR^a$, $CO_2R^a$, $CO_2NR^aR^a$, $NR^aR^b$ and $NH(=NH)NH_2$;

$R^{10}$ is independently at each occurrence selected from $C_1$-$C_{24}$-alkyl, $C_3$-$C_{24}$-alkenyl, $C_3$-$C_{24}$-alkynyl, $C_0$-$C_4$-alkylene-$C_3$-$C_7$-cycloalkyl or $C_0$-$C_4$-alkylene-aryl;

wherein any aryl group is phenyl, naphthyl or tetrahydronaphthyl and wherein any phenyl, alkyl, alkyne, alkene, alkylene, cycloalkyl, naphthyl group or tetrahydronaphthyl is optionally substituted with from 1 to 4 substituents selected from: halo, nitro, cyano, $NR^aR^a$, $NR^aS(O)_2R^a$, $NR^aC(O)R^a$, $NR^aCONR^aR^a$, $NR^aCO_2R^a$, $OR^a$; $SR^a$, $SO_3R^a$, $SO_2R^a$, $SO_2NR^aR^a$, $CO_2R^a$ $C(O)R^a$, $CONR^aR^a$, $CR^aR^a$ $NR^aR^a$, $C_1$-$C_4$-alkyl, $C_2$-$C_4$-alkenyl, $C_2$-$C_4$-alkynyl and $C_1$-$C_4$-haloalkyl;

wherein $R^a$ is independently at each occurrence selected from: H and $C_1$-$C_4$-alkyl; and $R^b$ is independently at each occurrence selected from: H, and $C_1$-$C_4$-alkyl, $C(O)$—$C_1$-$C_4$-alkyl, $S(O)_2$—$C_1$-$C_4$-alkyl.

Surprisingly, the 3'-cladribine phosphoramidates of the invention tend to be more potent than the corresponding 5'-cladribine ProTides. This is contrary to the trend observed more generally for other nucleosides.

Certain 3'-cladribine phosphoramidates of the invention have been shown to target cancer stem cells.

The potency of 3'-cladribine phosphoramidates of the invention in mycoplasma infected cells is reduced by smaller amount than both cladribine and 5'-cladribine ProTides.

In an embodiment, the compound of formula (I) is a compound of formula (II):

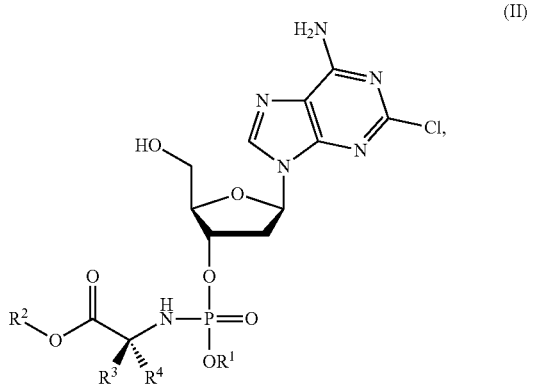

(II)

wherein $R^1$, $R^2$, $R^3$ and $R^4$ are as described above for compounds of formula (I).

The following statements apply to compounds of formula (I) or (II). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

It may be that $R^1$ is substituted or unsubstituted phenyl. It may be that $R^1$ is substituted or unsubstituted naphthyl (e.g. 1-naphthyl).

Preferably, $R^1$ is unsubstituted. Thus, $R^1$ may be unsubstituted phenyl or unsubstituted naphthyl (e.g. 1-naphthyl). Thus, $R^1$ may be unsubstituted phenyl. Alternatively, $R^1$ may be unsubstituted naphthyl (e.g. 1-naphthyl). $R^1$ may be tetrahydronaphthyl.

$R^2$ may be selected from $C_2$-$C_{10}$-alkyl, $C_5$-$C_7$-cycloalkyl or $CHR^{11}$-phenyl; wherein $R_{11}$ is selected from H and $C_1$-$C_4$-alkyl. The $R^2$ groups may be unsubstituted.

$R^2$ is preferably selected such that it comprises five or more carbon atoms. $R^2$ may therefore be selected such that it includes six or more carbon atoms. $R^2$ is preferably selected such that it comprises only carbon and hydrogen atoms. $R^2$ may be selected from $C_5$-$C_7$-cycloalkyl, $C_5$-$C_8$-alkyl and benzyl, optionally wherein said groups are unsubstituted.

$R^2$ may be $C_2$-$C_{10}$-alkyl. $R^2$ may be $C_4$-$C_8$-alkyl. Thus, $R^2$ may be selected from iso-butyl, tert-butyl, n-butyl, n-pentyl, $CH_2C(Me)_3$ or n-hexyl.

$R^2$ may be $C_5$-$C_7$-cycloalkyl. Thus, $R^2$ may be cyclohexyl.

$R^2$ may be $CHR^{11}$-phenyl; wherein $R_{11}$ is selected from H and $C_1$-$C_4$-alkyl. $R^2$ may be benzyl.

$R^2$ is preferably unsubstituted.

It may be that one of $R^3$ and $R^4$ is H and the other is selected such that it is a side chain of an amino acid selected from: glycine, alanine, valine, leucine, isoleucine, phenylalanine, methionine, histidine, serine, cysteine, glutamic acid, aspartic acid, asparagine, glutamine, arginine, lysine, threonine, tyrosine and tryptophan. It may be that one of $R^3$ and $R^4$ is H and the other is selected such that it is a side chain of an amino acid selected from: glycine, alanine, valine, leucine, isoleucine and phenylalanine. It may be that one of $R^3$ and $R^4$ is H and the other is selected such that it is a side chain of an amino acid selected from: alanine, valine, leucine, isoleucine and phenylalanine.

It may be that $R^4$ is H and $R^3$ is selected such that it is a side chain of an amino acid selected from: glycine, alanine, valine, leucine, isoleucine, phenylalanine, methionine, histidine, serine, cysteine, glutamic acid, aspartic acid, asparagine, glutamine, arginine, lysine, threonine, tyrosine and tryptophan. It may be that $R^4$ is H and $R^3$ is selected such that it is a side chain of an amino acid selected from: glycine, alanine, valine, leucine, isoleucine and phenylalanine. It may be that $R^4$ is H and $R^3$ is selected such that it is a side chain of an amino acid selected from: alanine, valine, leucine, isoleucine and phenylalanine. Thus the amino acid ($NH_2CR^3R^4CO_2H$) from which the phosphoramidate moiety is derived may be the L-amino acid.

It may be that $R^4$ is H. It may be that $R^3$ is selected from H, $C_1$-$C_6$-alkyl and $C_1$-$C_3$-alkylene-$R^9$. It may be that $R^3$ is selected from $C_1$-$C_6$-alkyl and $C_1$-$C_3$-alkylene-$R^9$. It may be that $R^9$ is phenyl.

It may be that one of $R^3$ and $R^4$ is H and the other is selected from: H, Me, isopropyl, isobutyl and benzyl. It may be that one of $R^3$ and $R^4$ is H and the other is selected from: Me, isopropyl, isobutyl and benzyl. It may be that one of $R^3$ and $R^4$ is H and the other is Me.

It may be that $R^4$ is H and $R^3$ is selected from: H, Me, isopropyl, isobutyl and benzyl. It may be that $R^4$ is H and $R^3$ is selected from: Me, isopropyl, isobutyl and benzyl. It may be that $R^4$ is H and $R^3$ is Me.

It may be that $R^3$ is $C_1$-$C_4$-alkyl. It may be that $R^3$ is selected from isopropyl, isobutyl and methyl. It may be that $R^3$ is $CH_2$-phenyl.

It may be that $R^3$ is H. It may be that $R^4$ is selected from H, $C_1$-$C_6$-alkyl and $C_1$-$C_3$-alkylene-$R^9$. It may be that $R^4$ is selected from $C_1$-$C_6$-alkyl and $C_1$-$C_3$-alkylene-$R^9$. It may be that $R^9$ is phenyl.

It may be that $R^4$ is $C_1$-$C_4$-alkyl. It may be that $R^4$ is selected from isopropyl, isobutyl and methyl. It may be that $R^4$ is $CH_2$-phenyl.

It may be that $R^4$ and $R^3$ are each methyl.

It may be that $R^4$ is H, $R^3$ is Me and $R^2$ is benzyl.

It may be that $R^5$ is $C_1$-$C_4$-alkyl. Preferably, however, $R^5$ is H.

It may be that $R^6$ is $C(O)R^{10}$. In this embodiment, $R^{10}$ may be $C_1$-$C_4$-alkyl.

Preferably, however, $R^6$ is H.

It may be that $R^7$ is $C_1$-$C_4$-alkyl. Preferably, however, $R^7$ is H.

It may be that $R^8$ is $C(O)R^{10}$. It may be that $R^8$ is $C(O)OR^{10}$. In these embodiments, $R^{10}$ may be $C_8$-$C_{24}$-alkyl. Preferably, however, $R^8$ is H.

Preferably, $R^7$ and $R^8$ are each H. Preferably, $R^5$, $R^6$, $R^7$ and $R^8$ are each H.

The compound of formula (I) may be a compound selected from:
2-Chloro-2'-deoxyadenosine-3'-[phenyl-(ethoxy-L-alaninyl)]-phosphate,
2-Chloro-2'-deoxyadenosine-3'-[phenyl-(tert-butoxy-L-alaninyl)]-phosphate,
2-Chloro-2'-deoxyadenosine-3'-[phenyl-(benzoxy-D-alaninyl)]-phosphate,
2-Chloro-2'-deoxyadenosine-3'-[phenyl-(benzoxy-glycinyl)]-phosphate,
2-Chloro-2'-deoxyadenosine-3'-[phenyl-(benzoxy-L-leucinyl)]-phosphate,
2-Chloro-2'-deoxyadenosine-3'-[1-naphthyl-(2,2-dimethylpropoxy-L-alaninyl)] phosphate,
2-Chloro-2'-deoxyadenosine-3'-[1-naphthyl-(pentoxy-L-leucinyl)]-phosphate,
2-Chloro-2'-deoxyadenosine-3'-[1-naphthyl-(cyclohexoxy-L-alaninyl)]-phosphate,
2-Chloro-2'-deoxyadenosine-3'-[phenyl-(cyclohexoxy-L-alaninyl)]phosphate,
2-Chloro-2'-deoxyadenosine-3'-[phenyl-(2,2-dimethylpropoxy-L-alaninyl)]phosphate,
2-Chloro-2'-deoxyadenosine-3'-[phenyl-(ethoxy-2,2-dimethylglycinyl)]-phosphate,
2-Chloro-2'-deoxyadenosine-3'-[phenyl-(benzoxy-L-phenylalaninyl)] phosphate,
2-Chloro-2'-deoxyadenosine-3'-[1-naphthyl-(benzoxy-L-phenylaninyl)] phosphate,
2-Chloro-2'-deoxyadenosine-3'-[phenyl-(benzoxy-L-valinyl)] phosphate,
2-Chloro-2'-deoxyadenosine-3'-[phenyl(iso-propoxy-L-alaninyl)] phosphate,
2-Chloro-2'-deoxyadenosine-3'-[phenyl-(2-butoxy-L-alaninyl)] phosphate,
2-Chloro-2'-deoxyadenosine-3'-[phenyl-((S)-1-phenylethoxy-L-alaninyl)-phosphate,
2-Chloro-2'-deoxyadenosine-3'-[1-naphthyl-(benzoxy-L-alaninyl) phosphate and
2-Chloro-2'-deoxyadenosine-3'-[phenyl-(benzoxy-L-alaninyl)-phosphate.

The compound of formula (I) may be a compound selected from:
2-Chloro-2'-deoxyadenosine-3'-[1-naphthyl-(benzoxy-L-alaninyl)-phosphate and
2-Chloro-2'-deoxyadenosine-3'-[phenyl-(benzoxy-L-alaninyl)-phosphate.

It may be that the compound of formula (I) is a free base.

The compounds of the invention comprise a chiral centre at the phosphorous atom. The compound may be present as a mixture of phosphate diastereoisomers, as the (S)-epimer at the phosphorus atom in substantially diastereomerically pure form or as the (R)-epimer at the phosphorus atom in substantially diastereomerically pure form. 'Substantially diastereomerically pure' is defined for the purposes of this invention as a diastereomeric purity of greater than about 90%. If present as a substantially diastereoisomerically pure form, the compound may have a diastereoisomeric purity of greater than 95%, 98%, 99%, or even 99.5%. Alternatively, the compound may be present as a mixture of phosphate diastereoisomers.

The (R)- and/or (S)-epimers of the compounds can be obtained in substantially diastereomerically pure form by chromatography, e.g. HPLC optionally using a chiral column. Alternatively, the (R)- and/or (S)-epimers of the compounds can be obtained in substantially diastereomerically pure form by crystallisation from an appropriate solvent or solvent system. In a further alternative, the (R)- and/or (S)-epimers of the compounds can be obtained in substantially diastereomerically pure form by coupling an appropriately protected cladribine derivative with a diastereomerically enriched phosphoramidate precursor and subsequently deprotecting. The (R)- and/or (S)-epimers of the compounds can be obtained in substantially diastereomerically pure form by direct synthesis, e.g. using the methods described in WO2014/076490.

According to a second aspect of the present invention, there is provided a compound of the first aspect for use in a method of treatment.

According to a third aspect of the present invention, there is provided a compound of the first aspect for use in the prophylaxis or treatment of cancer.

According to a fourth aspect of the present invention there is provided use of a compound of the first aspect in the manufacture of a medicament for the prophylaxis or treatment of cancer.

According to a fifth aspect of the present invention, there is provided a method of prophylaxis or treatment of cancer comprising administration to a patient in need of such treatment an effective dose of a compound of the first aspect.

Each of the third, fourth and fifth aspects of the invention can comprise embodiments for treating cancer employed in combination with other cancer therapy. Examples of other cancer therapy include radiotherapy and/or other chemotherapy.

With respect to each of the third, fourth and fifth aspects of the present invention, embodiments of the invention comprise a cancer selected from among haematological and solid tumours. In particular, the cancer can be selected from the group consisting of leukaemia, multiple myeloma, lung cancer, liver cancer, breast cancer, head and neck cancer, neuroblastoma, thyroid carcinoma, skin cancer (including melanoma), oral squamous cell carcinoma, urinary bladder cancer, Leydig cell tumour, colon cancer, colorectal cancer and gynaecological cancers, including ovarian cancer, uterine cancer and cervical cancer, including epithelia cervix carcinoma. In preferred embodiments, the cancer is leukaemia and can be selected from the group consisting of acute lymphoblastic leukaemia, acute myelogenous leukaemia (also known as acute myeloid leukaemia or acute nonlymphocytic leukaemia), acute promyelocytic leukaemia, acute lymphocytic leukaemia, chronic myelogenous leukaemia (also known as chronic myeloid leukaemia, chronic myelocytic leukaemia or chronic granulocytic leukaemia), chronic lymphocytic leukaemia, monoblastic leukaemia and hairy cell leukaemia. In further preferred embodiments, the cancer is acute lymphoblastic leukaemia.

Certain compounds embodying the present invention have been found to have enhanced anti-cancer activity, compared to the 5'-cladribine ProTides, in treating solid tumours, as well as leukaemia. Examples of solid tumours that are suitable for treatment by compounds of the present invention include breast cancer, prostate cancer, lung cancer, colon cancer, cervical cancer and lymphomas. Examples of lymphomas suitable for treatment by compounds of the invention include Hodgkin Lymphoma and non-Hodgkin Lymphoma. Examples of leukaemia which are suitable for treatment by compounds of the present invention include myeloid leukaemia, multiple myeloma, chronic myelogenous leukaemia, acute myelogenous leukaemia and acute lymphocytic leukaemia.

The compound of the invention may be for use in treating cancer in a patient with mycoplasma infected cells. Thus, the invention may provide a method of treating cancer in a patient with mycoplasma infected cells. Typically, the mycoplasma infected cells will be mycoplasma infected cancer cells.

The invention provides a compound of the invention for use in targeting cancer stem cells.

The invention provides the use of a compound of the invention in the manufacture of a medicament for targeting cancer stem cells.

The invention provides a method of targeting cancer stem cells, the method comprising providing a population of cancer stem cells with an amount of a compound of the invention sufficient to target such cancer stem cells.

The targeting of cancer stem cells referred to in the present invention may be employed in the prevention or treatment of cancer. In such embodiments the population of cancer stem cells may be in a cancer or pre-cancerous condition in a patient in need of such targeting, and the method may comprise administering a therapeutically effective amount of a compound of the invention to the patient.

The invention provides a compound of the invention for use as an anti-cancer stem cell medicament. This use of a compound of the invention may also be employed in the prevention or treatment of cancer.

The invention provides a method of determining whether a patient with cancer or a pre-cancerous condition will benefit from prevention or treatment of cancer with a compound of the invention, the method comprising:
assaying a biological sample representative of cancer or a pre-cancerous condition in the patient for the presence of cancer stem cells; wherein the presence of cancer stem cells in the biological sample indicates that the patient will benefit from treatment with a compound of the invention.

The invention provides a method of determining a suitable treatment regimen for a patient with cancer or a pre-cancerous condition, the method comprising:
assaying a biological sample representative of cancer or a pre-cancerous condition in the patient for the presence of cancer stem cells; wherein the presence of cancer stem cells in the biological sample indicates that a suitable treatment regimen will comprise treatment of the patient with a compound of the invention.

The invention provides a compound of the invention for use in the prevention or treatment of cancer in a patient selected for such treatment by a method comprising:
assaying a biological sample representative of cancer or a pre-cancerous condition in the patient for the presence of cancer stem cells; wherein the presence of cancer stem cells in the biological sample indicates that the patient is suitable for treatment with a compound of the invention.

The methods set out above may further comprise a step of preventing or treating the cancer or pre-cancerous condition using a compound of the invention.

In suitable embodiments of the methods of the invention the cancer is relapsed or refractory cancer. A compound of the invention may be used for the treatment of such relapsed or refractory cancer.

The invention provides a compound of the invention for use in treatment of refractory cancer in a subject. The subject may be a human patient.

The invention provides the use of a compound of the invention in the manufacture of a medicament for the treatment of relapsed or refractory cancer in a human patient.

The invention provides a method of treating relapsed or refractory cancer in a subject, the method comprising providing a therapeutically effective amount of a compound of the invention to a subject in need of such treatment.

According to further aspects of the present invention, there are provided a compound of the present invention for use in a method of prophylaxis or treatment, a use of a compound of the present invention in the manufacture of medicament for use in a method of prophylaxis or treatment and a method of prophylaxis or treatment of a patient comprising administration to a patient in need thereof a compound of the present invention, wherein, in each instance, the method of prophylaxis or treatment comprises a method of prophylaxis or treatment of myelodysplastic syndrome.

According to a sixth aspect of the invention, there is provided a pharmaceutical composition comprising a compound of the first aspect, in combination with a pharmaceutically acceptable excipient.

According to a seventh aspect of the present invention, there is provided a method of preparing a pharmaceutical composition comprising the step of combining a compound of the first aspect with a pharmaceutically acceptable excipient.

Various aspects of the invention are based upon the finding that a compound of the invention is able to preferentially reduce cancer stem cell numbers. This finding is surprising in that cancer stem cells are known to be resistant to many chemotherapeutic agents, and there has previously been no suggestion that either a compound of the invention or cladribine, the parent compound from which a compound of the invention is derived, were able to target cancer stem cells. Thus the finding that a compound of the invention is able to target cancer stem cells and thus reduce their numbers, a finding which the inventors have confirmed is applicable across a broad range of cancers, represents a surprising breakthrough that enables a range of new therapeutic applications of a compound of the invention.

DETAILED DESCRIPTION

The compounds in the formulations of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. Preferably, the compounds of the invention are not in the form of a salt, i.e. they are in the form of the free base/free acid.

The term $C_m$-$C_n$ refers to a group with m to n carbon atoms.

The term "alkyl" refers to a linear or branched saturated hydrocarbon group. An alkyl group is monovalent. For example, $C_1$-$C_6$-alkyl may refer to methyl, ethyl, n-propyl, iso-propyl, n-butyl, sec-butyl, tert-butyl, n-pentyl and n-hexyl. The alkyl groups are preferably unsubstituted.

The term "cycloalkyl" refers to a cyclic saturated hydrocarbon group. An alkyl group is monovalent. For example, $C_6$-$C_7$-cycloalkyl may refer cyclopentyl, cyclohexyl or cycloheptyl. The cycloalkyl groups are preferably unsubstituted.

The term "alkylene" refers to a linear saturated hydrocarbon chain. An alkylene group is divalent. For example, $C_1$-alkylene may refer to a $CH_2$ group. $C_2$-alkylene may refer to —$CH_2CH_2$— group. The alkylene groups are preferably unsubstituted.

The term "alkenyl" refers to a branched or linear hydrocarbon chain containing at least one carbon-carbon double bond. The double bond(s) may be present as the E or Z isomer. The double bond may be at any possible position of the hydrocarbon chain. For example, "$C_2$-$C_4$-alkenyl" may refer to ethenyl, allyl and butenyl. The alkenyl groups are preferably unsubstituted.

The term "alkynyl" refers to a branched or linear hydrocarbon chain containing at least one carbon-carbon triple bond. The triple bond may be at any possible position of the hydrocarbon chain. For example, "$C_2$-$C_6$-alkynyl" may refer to ethynyl, propynyl, butynyl. The alkynyl groups are preferably unsubstituted.

The term "aryl" refers to phenyl groups, naphthyl groups and tetrahydronaphthyl groups. The term "aryl" may refers to phenyl groups or naphthyl groups. The aryl groups (e.g. the naphthyl or phenyl groups) may be unsubstituted.

The present invention also includes all pharmaceutically acceptable isotopically-labelled forms of compounds wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^3H$, and carbon-14, i.e. $^{14}C$, and $^{18}F$ are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds can generally be prepared by conventional techniques known to those skilled in the art or by processes analogous to those described using an appropriate isotopically-labelled reagent in place of the non-labelled reagent previously employed.

The compounds of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered parenterally, then the dosage of the compound of the invention may be in the range from 0.1 to 5 g/m², e.g. from 0.5 to 2 g/m². The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient.

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

For oral administration, the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For parenteral (e.g. intravenous) administration the compounds of the invention may be administered as a sterile aqueous or oily solution. The compounds of the invention are very lipophilic. Aqueous formulations may, therefore, also contain a pharmaceutically acceptable polar organic solvent.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient.

The method of treatment or the compound for use in the treatment of cancer may involve, in addition to the compound of the invention, conventional surgery or radiotherapy or chemotherapy. Such chemotherapy may include the administration of one or more other active agents.

Where a further active agent is administered as part of a method of treatment of the invention, such combination treatment may be achieved by way of the simultaneous, sequential or separate dosing of the individual components of the treatment. Such combination products employ the compounds of this invention within a therapeutically effective dosage range described hereinbefore and the one or more other pharmaceutically-active agent(s) within its approved dosage range.

Thus, the pharmaceutical formulations of the invention may comprise another active agent.

The one or more other active agents may be one or more of the following categories of anti-tumour agents:

(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); proteasome inhibitors, for example carfilzomib and bortezomib; interferon therapy; platins (such as cicplatin and carboplatin); and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (Cl 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin-dependent kinase inhibitors such as CDK2 and/or CDK4 inhibitors;

(v) antiangiogenic agents such as those which inhibit the effects of vascular endothelial growth factor, for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and
(viii) cytotoxic agents for example fludaribine (fludara), cladribine, pentostatin (Nipent™);
(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;
(x) targeted therapies, for example PI3Kd inhibitors, for example idelalisib and perifosine; or compounds that inhibit PD-1, PD-L1 and CAR T.

The one or more other active agents may also be antibiotics.

"Cancer Stem Cells"

Cancer stem cells, which are sometimes otherwise referred to as "tumour initiating cells", are well known to those skilled in the art. As used herein, the term "cancer stem cell" is to be interpreted in accordance with its widely accepted meaning, which is a cell that possesses the capacity to self-renew through asymmetric division, to initiate tumour formation, and to give rise to more mature non-stem cell cancer progeny by differentiation.

Cancer stem cells play a major role in the development, progression, recurrence and propagation of cancers. Accordingly, the finding that compounds of the invention are able to target cancer stem cells, and thereby reduce their numbers, offers therapeutic possibilities in preventing or treating these activities.

As discussed in more detail elsewhere in the specification, cancer stem cells are found in pre-cancerous conditions, where their presence is believed to contribute to the development of such conditions into cancers. Accordingly the methods of treatment and medical uses of the invention, in which a compound of the invention is used to target cancer stem cells, may be used to reduce cancer stem cell numbers in pre-cancerous conditions (such as myelodysplastic syndrome, or other conditions considered elsewhere in the specification), and thus to prevent progression of such pre-cancerous conditions into cancer.

As referred to above, asymmetric cell division of cancer stem cells gives rise to differentiated non-stem cancer cells. Thus cancer stem cells are responsible for the formation and maintenance of the bulk of the tumour.

The accumulation of such non-stem cancer cells plays a major role in the progression of cancers. Targeting of cancer stem cells by a compound of the invention is able to reduce cancer stem cell numbers, which in turn reduces the number of non-stem cancer cell progeny. Thus methods of treatment and medical uses of a compound of the invention in accordance with the present invention are of benefit in treating cancer by preventing cancer progression. Such embodiments are described in more details elsewhere in the present specification.

Cancer stem cells are also able to act as a reservoir of cancer cells that they may cause the recurrence of cancer after remission. Even in the event that the majority of a patient's cancer cells have been removed (for example by surgery, radiotherapy, or chemotherapy, either alone or in combination), so that no observable signs of a cancer remain, the continued presence of cancer stem cells may nucleate the recurrence of the cancer over time. Targeting of cancer stem cells by a compound of the invention provides a new mode by which cancer stem cell numbers may be reduced and cancer stem cells killed. Accordingly, and as discussed in more detail elsewhere in the specification, in suitable embodiments the present invention provides methods and medical uses in which a compound of the invention prevents or delays recurrence of cancer.

Furthermore, movement of cancer stem cells from the site of a cancer to another location within the body can contribute to propagation of cancer, for example by giving rise to metastases. Consequently, the ability of a compound of the invention to target cancer stem cells therefore provides new methods of treatment and medical uses in preventing or treating cancer propagation.

In addition to their biological activities, cancer stem cells may be identified by their expression of certain characteristic cell surface markers. Cancer stem cells identified in haematological malignancies are typically $CD34^+$, while in solid tumours, $CD44^+$, $CD133^+$ and $CD90^+$ have been identified as cancer stem cell markers. The following table summarises examples of known cancer stem cell surface phenotypes. It is expected that each of these forms of cancer stem cell can be targeted using a compound of the invention in accordance with the invention, and so methods or uses employing a compound of the invention may be used in the prevention or treatment of cancers associated with cancer stem cells expressing any of these sets of markers.

| Tumour type | Reported cell surface markers for cancer stem cells |
|---|---|
| Solid Tumours | |
| Breast | $CD44^+/CD24^{-/low}/Lineage^-/ESA^+$ |
| CNS | $CD133^+$ |
| Colon | $CD133^+$ |
| Colon | $ESA^{high}/CD44^+/Lineage^-/(CD166^+)$ |
| Ewing's | $CD133^+$ |
| Head and Neck | $CD44^+/Lineage^-$ |
| Melanoma | $ABCB5^+$ |
| Liver | $CD90^+/CD45^-/(CD44^+)$ |
| Cholangiocarcinoma | $CD44^+/GLI1^+$ (Glioma-associated oncogene homolog-1) |
| Ovarian | $CD44^+/CD117^+$ |
| Pancreas | $CD44^+/CD24^+/ESA^+$ |
| Pancreas | $CD133^+$ |
| Non-small-cell lung cancer | $CD44^+/Ber-EP4^+$ |
| Bladder cancer | $CD44^+/ALDH1A1^+$ |

-continued

| Tumour type | Reported cell surface markers for cancer stem cells |
|---|---|
| Haematological tumours | |
| Acute myeloid leukaemia | Lin$^-$/CD34$^+$/CD38$^-$/CD123$^+$ |
| B-Acute lymphoblastic leukaemia | CD34$^+$/CD10$^-$ or CD34$^+$/CD19$^-$ |
| B-Acute lymphoblastic leukaemia | CD34$^+$/CD38$^-$/CD19$^+$ |
| Multiple myeloma | CD34$^-$/CD138$^-$ |
| T-Acute lymphoblastic leukaemia | CD34$^+$/CD4$^-$ or CD34$^+$/CD7$^-$ |

The data presented in the Examples demonstrate that a compound of the invention is able to target cancer stem cells of leukaemic stem cell lines, specifically cancer stem cells present in the acute myeloid leukaemia cell line KG1a. This cell line manifests a minor stem cell-like compartment with a distinct immunophenotype (Lin$^-$/CD34$^+$/CD38$^-$/CD123$^+$) which is targeted by a compound of the invention. Accordingly, methods of treatment or medical uses of a compound of the invention in accordance with the present invention may be used to prevent or treat leukaemia or other cancers associated with cancer stem cells expressing these characteristic markers.

The present invention also provides methods and medical uses in which patients are selected for prevention or treatment of cancer, utilising a compound of the invention, on the basis of the identification of the presence of cancer stem cells in a biological sample representative of the patient's cancer or pre-cancerous condition. The markers set out above provide suitable examples that can be used to identify the presence of cancer stem cells in accordance with such embodiments of the invention. Suitable techniques by which expression of these markers may be investigated in a biological sample are considered further elsewhere in this specification.

"Targeting of Cancer Stem Cells"

The present invention provides the first indication that compounds of the invention can be used for targeting cancer stem cells. The ability of compounds of the invention to target cancer stem cells is illustrated in the Examples disclosed in this specification.

It can be seen from the Examples that when a compound of the invention is provided to populations of cancer cells containing cancer stem cells it targets the cancer stem cells present, leading to a reduction in the total number of cancer cells and in the proportion of total cancer cells exhibiting phenotypic markers of cancer stem cells.

While the parent prodrug compound cladribine is able to target cancer stem cells at certain, higher, concentrations, the compounds of the invention demonstrate the ability to achieve such targeting across a broader range of concentrations. Notably, in vitro studies, the results of which are reported in the present application, demonstrate that the compounds of the invention are able to target cancer stem cells at low concentrations more effectively than cladribine. At certain concentrations, the improvement in cancer stem cell targeting is such that the proportion of cancer stem cells remaining in a population of cells treated with a compound of the invention is significantly lower than for a population of cells treated with cladribine. It will be appreciated that the ability to achieve effective targeting of cancer stem cells at low concentrations of cytotoxic agents will generally be desirable since this reduces the likelihood of unwanted side effects.

It is believed that the compounds of the invention possess enhanced cellular membrane permeability (as compared to cladribine), and that this contributes to the enhanced anti-cancer potency of the compounds of the invention compared to the parent nucleoside from whom they are derived.

Without wishing to be bound by any hypothesis, the inventors believe that the reduction in cancer stem cell numbers arises as a result of targeted killing of the cancer stem cells among the cancer cell population. That is to say, that compounds of the invention appear to kill cancer stem cells preferentially as compared to killing of non-stem cancer cells, thereby causing the death of cancer stem cells, and a reduction of the proportion of cancer stem cells among the total cancer cell population.

While the inventors believe that compounds of the invention preferentially kill cancer stem cells as compared to non-stem cancer cells, other mechanisms may also contributed to the reduction in the proportion of cancer stem cells caused by a compound of the invention's targeting of these cells.

Merely by way of example, treatment with a compound of the invention may cause an increase in cancer stem cell differentiation, thereby reducing cancer stem cell numbers and also the proportion of total cancer cells represented by cancer stem cells. Alternatively, a compound of the invention may cause cancer stem cells to lose their stem cell phenotype, for example losing their ability to self-renew, thereby reducing cancer stem cell numbers.

References to targeting of cancer stem cells in the present disclosure should be interpreted accordingly. For the purposes of the present disclosure, "targeting" of cancer stem cells may be taken as encompassing any mechanism by which a compound of the invention reduces the proportion of cancer stem cells present in a population of cells, whether in vitro or in vivo. In particular targeting of cancer stem cells may be taken as encompassing preferential killing of cancer stem cells as compared to other cell types, particularly as compared to non-stem cancer cells.

"Prevention or Treatment of Cancer"

The invention provides medical uses and methods of treatment in which a compound of the invention is used for the prevention or treatment of cancer. In the context of the present invention, "prevention" of cancer is to be considered as relating to prophylactic applications of a compound of the invention used before the development of cancer, and with an aim of stopping cancer from developing. On the other hand "treatment" of cancer is taken as concerning the use of a compound of the invention after cancer has occurred, with a view to ameliorating cancer by slowing or stopping cancer cell proliferation and tumour growth. Advantageously treatment of cancer may cause partial or total reduction in cancer cell numbers and tumour size. Effective treatment of cancer may bring about disease that either "stabilizes" or "responds" in accordance with the RECIST (Response Evaluation Criteria In Solid Tumours) rules.

As described in more detail below, prevention of cancer in accordance with the present invention may be of particular benefit in patients who have a pre-cancerous condition that increases their likelihood of developing cancer.

"Prevention of Cancer"

Prevention of cancer in accordance with the present invention may be effected by treatment of a pre-cancerous condition using a compound of the invention in accordance with the various aspects or embodiments of the invention described herein.

In particular, prevention of cancer, in the context of the present invention, may be achieved by the methods or medical uses of the invention in which a compound of the invention is provided to a patient with a pre-cancerous condition. Methods of treatment or medical uses in accordance with this embodiment may prevent development of the treated pre-cancerous condition into cancer, thereby providing effective prevention of cancer.

References to prevention of cancer in the context of the present invention may also encompass other prophylactic applications of a compound of the invention. For example, the ability of a compound of the invention to target cancer stem cells and thereby prevent the development of cancer, and/or prevent the progression of cancer, and/or prevent the recurrence of cancer, and/or prevent the propagation of cancer.

"Pre-Cancerous Conditions"

Cancer is frequently preceded by the development of a pre-cancerous condition, which is not itself cancerous, but is associated with an increased risk of cancer. Accumulation of genetic or epigenetic changes may cause previously normal cells to develop a cancer stem cell phenotype. Accordingly, cancer stem cells may also be present in such pre-cancerous conditions, as well as in cancerous conditions.

It is believed that the presence of cancer stem cells in pre-cancerous conditions contributes to the development of these conditions into cancer. The methods and medical uses of the invention may be employed to target cancer stem cells present in pre-cancerous conditions, and thereby treat such conditions. It will be appreciated that the new and unexpected finding that compounds of the invention target cancer stem cells means that treatment of pre-cancerous conditions with such compounds may be used to prevent the treated conditions developing into cancer. This represents a way in which a compound of the invention can be used medically in the prevention of cancer, as considered elsewhere in this specification.

Examples of pre-cancerous conditions that may be treated in accordance with the present invention include, but are not limited to, those selected from the group consisting of: actinic keratosis, Barrett's oesophagus, atrophic gastritis, dyskeratosis congenital, Sideropenic dysphagia, Lichen planus, oral submucous fibrosis, solar elastosis, cervical dysplasia, leukoplakia, erythroplakia, monoclonal gammopathy of unknown significance (MGUS), monoclonal B-cell lymphocytosis (MBL), myelodysplastic syndromes, as well as pre-cancerous conditions of the stomach such as atrophic gastritis, gastric ulcer, pernicious anaemia, gastric stumps, gastric polyps, and Menetrier's disease. Among the listed pre-cancerous conditions of the stomach, atrophic gastritis, pernicious anaemia, gastric stumps, and certain types of gastric polyp may have particularly heightened risk of developing into cancers.

Pre-cancerous conditions often take the form of lesions comprising dysplastic or hyperplastic cells. Accordingly, the presence of dysplasia or hyperplasia, as an alternative or addition to the presence of cells with expressed markers or phenotypes characteristic of cancer stem cells, may be used in the identification of pre-cancerous conditions.

The severity of dysplasia can vary between different pre-cancerous conditions, or with the development of a single pre-cancerous condition over time. Generally, the more advanced dysplasia associated with a pre-cancerous condition is, the more likely it is that the pre-cancerous condition will to develop into cancer. Dysplasia is typically classified as mild, moderate or severe. Severe dysplasia usually develops into cancer if left untreated. Suitably, methods of treatment or medical uses employing a compound of the invention may therefore be used to treat a patient with a pre-cancerous condition associated with severe dysplasia.

In a suitable embodiment of the invention a compound of the invention is used to treat a patient with severe cervical dysplasia. Severe cervical dysplasia may be diagnosed by means of a smear test. In another embodiment of the invention a compound of the invention is used to treat severe oesophageal dysplasia ("Barrett's oesophagus"). Severe oesophageal dysplasia may be diagnosed following a tissue biopsy.

It has recently been reported that pre-malignancies can also be identified by detecting somatic mutations in cells in individuals not known to have cancer. In particular, it has been reported that age-related clonal haematopoiesis is a common pre-malignant condition that is associated with increased overall mortality and increased risk of cardiometabolic disease. The majority of mutations detected in blood cells occurred in three genes: DNMT3A, TET2, and ASXL1. Accordingly, patients that will benefit from the use of a compound of the invention to target cancer stem cells, and thereby treat a pre-cancerous condition, may be identified by assaying a sample comprising blood cells for the presence of genetic mutations indicative of a pre-cancerous condition in at least one of: DNMT3A and/or TET2 and/or ASXL1.

Pre-cancerous conditions that may benefit from treatment with a compound of the invention in accordance with the invention to target cancer stem cells may also be identified by determination of the presence of cancer stem cells with reference to any of the techniques based upon expression of markers characteristic of cancer stem cells, or cancer stem cell phenotypes, discussed elsewhere in the specification.

"Treatment of Cancer"

The skilled person will appreciate that there are many measurements by which "treatment" of cancer may be assessed. Merely by way of example, any reduction or prevention of cancer development, cancer progression, cancer recurrence, or cancer propagation may be considered to indicate effective treatment of cancer.

In certain embodiments, a compound of the invention may be used: to reduce the proportion of cancer stem cells in a population of cancer cells; and/or to inhibit tumour growth; and/or to reduce tumourigenicity; and/or to prevent or treat a primary cancer; and/or to prevent or treat a relapsed cancer; and/or to prevent or treat a metastatic or secondary cancer; and/or to treat, prevent or inhibit metastasis or recurrence; and/or to treat or prevent refractory cancer.

The ability of cancer treatment using a compound of the invention to bring about a reduction in tumour size and also to maintain the reduction in tumour size during/after the period in which the treatment is administered represents a particularly relevant indication of effective cancer treatment. As set out in the Examples, the treatments or medical uses of the invention have proven surprisingly effective in this respect, even in models using cells representative of relapsed or refractory cancers that have previously been resistant to treatment with other therapies.

The data presented in the Examples illustrate that treatment with a compound of the invention reduces the proportion of cancer stem cells in a population of cancer cells. Characteristic biological activities or cell surface markers by which cancer stem cells may be identified are described elsewhere in the specification. In a suitable embodiment, treatment of cancer in accordance with the present invention may give rise to a reduction in the proportion of cancer stem cells present in a patient's cancer of at least 10%, at least 20%, at least 30%, or at least 40%. In suitable embodiments treatment of cancer in accordance with the invention may give rise to a reduction in the proportion of cancer stem cells present in a patient's cancer of at least 50%, at least 60%, at least 70%, or at least 80%. Treatment of cancer in accordance with the invention may give rise to a reduction in the proportion of cancer stem cells present in a patient's cancer of at least 85%, at least 90%, or at least 95%. Indeed, treatment of cancer in accordance with the invention may give rise to a reduction in the proportion of cancer stem cells present in a patient's cancer of at least 96%, at least 97%, at least 98%, at least 99%, or even 100% (such that substantially no cancer stem cells remain).

Asymmetric division of cancer stem cells contributes to the growth of tumours. Treatment of cancer with a compound of the invention in accordance with the present invention may bring about an inhibition of tumour growth of at least 10%, at least 20%, at least 30%, or at least 40%. Suitably treatment of cancer in accordance with the invention may give rise to an inhibition of tumour growth of at least 50%, at least 60%, at least 70%, or at least 80%. Treatment of cancer in accordance with the invention may give rise to an inhibition of tumour growth of at least 85%, at least 90%, or at least 95% in a patient so treated. Indeed, treatment of cancer in accordance with the invention may give rise to an inhibition of tumour growth of at least 96%, at least 97%, at least 98%, at least 99%, or even 100% in a treated cancer.

Tumour growth may be assessed by any suitable method in which the change in size of a tumour is assessed over time. Suitably the size of a tumour prior to cancer treatment may be compared with the size of the same tumour during or after cancer treatment. A number of ways in which the size of a tumour may be assessed are known. For example, the size of a tumour may be assessed by imaging of the tumour in situ within a patient. Suitable techniques, such as imaging techniques, may allow the volume of a tumour to be determined, and changes in tumour volume to be assessed.

As shown in the results set out in the Examples of this specification, the methods of treatment and medical uses of a compound of the invention of the invention are able not only to arrest tumour growth, but are actually able to bring about a reduction in tumour volume in patients with cancers, including patients with relapsed or refractory cancers. Suitably treatment of cancer in accordance with the present invention may give rise to a reduction in tumour volume of at least 10%, at least 20%, at least 30%, or at least 40%. In suitable embodiments, treatment of cancer in accordance with the invention may give rise to a reduction in tumour volume of at least 50%, at least 60%, at least 70%, or at least 80%. Treatment of cancer in accordance with the invention may give rise to a reduction in tumour volume of at least 85%, at least 90%, or at least 95%. Indeed, treatment of cancer in accordance with the invention may give rise to a reduction in tumour volume of at least 96%, at least 97%, at least 98%, at least 99%, or even 100%.

A reduction in tumour volume of the sort described above can be calculated with reference to a suitable control. For example in studies carried out in vitro, or in vivo in suitable animal models, the reduction in tumour volume may be determined by direct comparison between the volume of a tumour treated with a compound of the invention and the volume of a control tumour (which may be untreated, or may have received treatment other than with a compound of the invention). It will be appreciated that such models requiring lack of treatment of a tumour may not be ethically acceptable in the context of clinical trials or therapeutic management of patients, and in this case a reduction in tumour volume may be assessed by comparing the volume of a treated tumour with the volume of the same tumour prior to treatment, or with a predicted volume that would have been attained by the tumour had no treatment been administered.

The methods of treatment and medical uses of a compound of the invention may bring about a reduction in biomarkers indicative of cancer. The reduction of such biomarkers provides a further assessment by which effective treatment of cancer may be demonstrated. Suitable examples of such biomarkers may be selected on the basis of the type of cancer to be treated: in the case of gynaecological cancers CA125 represents a suitable example of a biomarker, while in the case of pancreatic or biliary cancers CA19.9 represents a suitable example of a biomarker, and in the case of colorectal cancers CEA may be a suitable biomarker.

Suitably treatment of cancer in accordance with the present invention may give rise to a reduction in cancer biomarkers of at least 10%, at least 20%, at least 30%, or at least 40%. In suitable embodiments, treatment of cancer in accordance with the invention may give rise to a reduction in cancer biomarkers of at least 50%, at least 60%, at least 70%, or at least 80%. Treatment of cancer in accordance with the invention may give rise to a reduction in cancer biomarkers of at least 85%, at least 90%, or at least 95%. Indeed, treatment of cancer in accordance with the invention may give rise to a reduction in cancer biomarkers of at least 96%, at least 97%, at least 98%, at least 99%, or even 100%.

Beneficial effects, such as a reduction in the proportion of cancer stem cells present, reduction in tumour growth, or reduction in tumour volume or cancer biomarkers, observed on treatment of cancer in accordance with the present invention may be maintained for at least one month. Suitably such beneficial effects may be maintained for at least two months, at least three months, at least four months, at least five months, or at least six months. Indeed, such beneficial effects may be maintained for at least 12 months, at least 18 months, or at least 24 months. Suitably the beneficial effects may be maintained for at least three years, at least four years, at least five years, at least six years, at least seven years, at least eight years, at least nine years, or for ten years or more.

In a suitable embodiment of the invention a compound of the invention is used in a method of preventing or treating cancer or a pre-malignant condition, by targeting cancer stem cells. In a suitable embodiment the invention provides the use of a compound of the invention in a method of preventing or treating cancer or a pre-malignant condition, wherein the method reduces the tumourigenicity of one or more cancer stem cells. Suitably such methods may prevent the progression of cancer, or inhibit tumour growth.

When a compound of the invention is used in methods or medical uses of the present invention to prevent or treat the progression of a cancer, such prevention or treatment may cause the cancer progression to be slowed, delayed or stopped entirely.

The progress of a cancer is typically determined by assigning a stage to the cancer. Staging is usually carried out by assigning a number from I to IV to the cancer, with I being an isolated cancer and IV being a cancer that has spread to the limit of what the assessment measures. Specifics of staging vary between cancers, but the stage generally takes into account the size of a tumour, whether it has invaded adjacent organs, how many regional (nearby) lymph nodes it has spread to (if any), and whether it has appeared in more distant locations (metastasised).

Generally, Stage I is localised to one part of the body and may be treated by surgical resection (for solid tumours that are small enough). Stage II is locally advanced, and is treatable by chemotherapy, radiation therapy, surgery, or a combination thereof. Stage III is also locally advanced and the designation of Stage II or Stage III depends on the specific type of cancer, although Stage III is generally accepted to be "late" locally advanced. Stage IV cancers have often metastasised to a second organ. Treatment of cancer using a compound of the invention in the methods or medical uses of the present invention may be used to treat a stage I, II, III or IV cancer by targeting cancer stem cells. Treatment with a compound of the invention may be used to prevent the progression of a cancer from one stage to the next. In one embodiment, treatment with a compound of the invention is used to prevent progression from Stage I to Stage II. In another embodiment, treatment with a compound of the invention is used to prevent progression from Stage II to Stage III. In still another embodiment, treatment with a compound of the invention is used to prevent progression from Stage III to Stage IV.

Preventing or inhibiting progression of the cancer is particularly important for preventing the spread of the cancer, for example the progression from Stage I to Stage II where the cancer spreads locally, or the progression from Stage III to Stage IV where the cancer metastasises to other organs. Cancer stem cells are tumourigenic and so are believed to play a critical role in the spread of cancer, both locally and metastatically. Methods of treatment or medical uses of the invention employing a compound of the invention can therefore be used to prevent the spread of cancer, by targeting tumourigenic cancer stem cells and thus reducing their numbers.

"Cancers"

Certain compounds of the invention demonstrate increased anti-cancer activity as compared to cladribine from which they are derived. This increase in anti-cancer activity appears to be provided as a result of increased activity against both cancer stem cells and non-stem cancer cells.

Cancer stem cells play a role in the biological activity of a wide range of cancers. Accordingly, there are a wide range of cancers that may be prevented or treated in accordance with the present invention.

As discussed elsewhere herein, cancer stem cells are known to be present in many tumour types including liquid tumours (including haematological tumours such as leukaemias and lymphomas) and solid tumours (such as breast, lung, colon, prostate, ovarian, skin, bladder, biliary and pancreas tumours). Methods of treatment and medical uses of a compound of the invention to target cancer stem cells are therefore expected to be useful in the prevention or treatment of such cancers.

Suitably a compound of the invention may be used in the prevention or treatment of a cancer selected from the group consisting of: leukaemia, lymphoma, multiple myeloma, lung cancer, liver cancer, breast cancer, head and neck cancer, neuroblastoma, thyroid carcinoma, skin cancer (including melanoma), oral squamous cell carcinoma, urinary bladder cancer, Leydig cell tumour, biliary cancer, such as cholangiocarcinoma or bile duct cancer, pancreatic cancer, colon cancer, colorectal cancer and gynaecological cancers, including ovarian cancer, endometrial cancer, fallopian tube cancer, uterine cancer and cervical cancer, including epithelia cervix carcinoma. In suitable embodiments, the cancer is leukaemia and can be selected from the group consisting of acute lymphoblastic leukaemia, acute myelogenous leukaemia (also known as acute myeloid leukaemia or acute non-lymphocytic leukaemia), acute promyelocytic leukaemia, acute lymphocytic leukaemia, chronic myelogenous leukaemia (also known as chronic myeloid leukaemia, chronic myelocytic leukaemia or chronic granulocytic leukaemia), chronic lymphocytic leukaemia, monoblastic leukaemia and hairy cell leukaemia. In further preferred embodiments, the cancer is acute lymphoblastic leukaemia. In a suitable embodiment the cancer is lymphoma, which may be selected from the group consisting of: Hodgkin's lymphoma; non-Hodgkin lymphoma; Burkitt's lymphoma; and small lymphocytic lymphoma.

Suitably targeting cancer stem cells in such cancers may achieve effective treatment of the cancer by preventing or treating the development of the cancer, by preventing or treating the progression of the cancer, by preventing or treating the recurrence of the cancer, or by preventing or treating the propagation of the cancer.

In a suitable embodiment the present invention provides a compound of the invention for use in targeting cancer stem cells in the prevention or treatment of metastatic cancer.

In a suitable embodiment the present invention provides a compound of the invention for use in targeting cancer stem cells in the treatment of relapsed or refractory cancer.

In a suitable embodiment the present invention provides a compound of the invention for use in targeting cancer stem cells in the treatment of a primary cancer. Suitably the primary cancer treated may be a second primary cancer.

The invention provides a compound of the invention for use in targeting cancer stem cells in the treatment of secondary cancer. In a suitable embodiment the secondary cancer is a metastatic cancer.

In a suitable embodiment the present invention provides a compound of the invention for use in targeting cancer stem cells, wherein the targeting of cancer stem cells prevents or inhibits: (i) recurrence of a cancer; (ii) occurrence of second primary cancer; or (iii) metastasis of a cancer.

Methods of treatment or medical uses in which a compound of the invention is employed on the basis of its ability to target cancer stem cells may be used in the treatment of relapsed or refractory cancer. The considerations regarding relapsed or refractory cancer in such embodiments are, except for where the context requires otherwise, the same as for the treatment of relapsed or refractory cancer in connection with the other aspects of the invention.

"Relapsed or Refractory Cancer"

As noted above, certain aspects and embodiments of the invention particularly relate to the use of a compound of the invention in the treatment of relapsed or refractory cancers.

For the purposes of the present invention, refractory cancers may be taken as cancers that demonstrate resistance to treatment by anti-cancer therapies other than those utilising a compound of the invention. For example, a compound of the invention may be used in the treatment of refractory cancers that are resistant to treatment with radiotherapy. Alternatively, or additionally, a compound of the invention may be used in the treatment of refractory cancers that are resistant to biological agents used in the treatment of cancer. In a suitable embodiment a compound of the invention may be used in the treatment of refractory cancers that are resistant to treatment with chemotherapeutic agents other than a compound of the invention.

In particular, refractory cancers that may benefit from the methods of treatment of medical uses of the invention employing a compound of the invention include those cancers that are resistant to cladribine.

Relapsed cancers (or recurrent cancers) are those that return after a period of remission during which the cancer cannot be detected. Cancer recurrence may occur at the site of the original cancer (local cancer recurrence), at a site close to that of the original cancer (regional cancer recurrence), or at a site distant from that of the original cancer (distal cancer recurrence). Cancer stem cells are believed to play a role in the recurrence of cancer, providing a source from which cells of the relapsed cancer are generated. Accordingly, the methods of treatment and medical uses of a compound of the invention in accordance with the invention, which enable targeting of cancer stem cells, may be of great benefit in the context of relapsed cancers. The ability of a compound of the invention to target cancer stem cells may be used to remove the populations of such cells that are able to give rise to recurrence, thus preventing incidences of relapsed cancer. The anti-cancer stem cell activity of a compound of the invention may also be used to target cancer stem cells in cancers that have recurred, as well as potentially exerting cytotoxic effects on non-stem cancer cells, thereby providing treatment of relapsed cancers.

In view of the above, it will be appreciated that a compound of the invention may be used in the methods or uses of the invention for the prevention or treatment of a relapsed cancer. A compound of the invention may be used in the methods or uses of the invention for the prevention or treatment of a local, regional or distant relapsed cancer.

A compound of the invention may be used in the methods or uses of the invention to prevent the recurrence of cancer by providing at least 2 months, at least 6 months, at least 12 months, at least 18 months, at least 24 months, or at least 30 months of remission. Indeed, a compound of the invention may be used to prevent recurrence of cancer by providing at least 4 years, at least 5 years, at least 6 years, at least 7 years, at least 8 years, at least 9 years, or at least 10 years of remission.

A compound of the invention may be used in the methods or uses of the invention to treat a relapsed cancer which has recurred after at least 2 months, at least 6 months, at least 12 months, at least 18 months, at least 24 months, or at least 30 months of remission. Indeed, a compound of the invention may be used to treat a relapsed cancer which has recurred after at least 4 years, at least 5 years, at least 6 years, at least 7 years, at least 8 years, at least 9 years, or at least 10 years of remission.

The ability of the compounds of the invention to target cancer stem cells gives rise to the ability of these compounds to prevent or treat cancers in accordance with the medical uses or methods of treatment of the invention. However, it should be noted that compounds of the invention also exert a direct cytotoxic effect upon non-stem cancer cells that make up the bulk of tumours. While activity of cancer stem cells may underlie much of the resistance that makes relapsed or refractory cancers so difficult to treat, non-stem cancer cells are also a major constituent of such relapsed or refractory cancers.

Certain compounds of the invention exert greater cytotoxic effects on non-stem cancer cells than does cladribine, the chemotherapeutic molecule from which the compounds of the invention are derived. Accordingly, the mechanism by which a compound of the invention acts in the treatment of relapsed or refractory cancer may not be limited solely to the anti-cancer stem cell activity of this compound, but may also make use of the action of a compound of the invention on non-stem cancer cells. In such uses treatment with a compound of the invention will reduce the total number of both cancer stem cells and non-stem cancer cells, but will preferentially reduce the proportion of cancer stem cells that remain after treatment.

Therapeutically Effective Doses of a Compound of the Invention

A therapeutically effective amount of a compound of the invention may be an amount sufficient to induce death of cancer cells. A therapeutically effective amount of a compound of the invention may be an amount sufficient to induce death of cancer stem cells. In some embodiments, particularly those relating to the treatment of relapsed or refractory cancer, a therapeutically effective amount of a compound of the invention may be an amount sufficient to induce death of cancer stem cells and also to induce death of non-stem cancer cells.

There are various different ways in which the amount of a therapeutically effective compound, such as a compound of the invention, to be administered to a patient may be calculated and expressed. One such way which is considered particularly relevant in doses of agents for the prevention or treatment of cancer, is in the amount of the agent to be administered per unit of body surface area of the patient. Such doses are typically expressed in terms of the amount of the agent (which may be determined by mass) per square meter ($m^2$) of surface area.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Examples

Example 1—Synthetic Procedures

Throughout this specification the following abbreviations have the indicate meanings:

| | |
|---|---|
| DCM—dichloromethane | DMF—N,N-dimethylformamide |
| TBDMS—tert-Butyldimethylsilyl | TFA—trifluoroacetic acid |
| THF—tetrahydrofuran | MeOH—methanol |
| br s—broad signal | tBuMgCl—tert-butyl magnesium Chloride |

5'-O-tert-Butyldimethylsilyl cladribine A

Cladribine (0.25 g, 0.88 mmol) was dissolved in anhydrous DMF (10 mL), TBDMSCl (0.15 g, 1.03 mmol) and imidazole (0.26 g, 3.82 mmol) was added under an argon atmosphere. The mixture was stirred at room temperature for 24 hours before water was added. The precipitate was filtered off and purified by silica gel column chromatography to give 3',5'-bis-O-tert-butyldimethylsilyl cladribine (0.12 g, 27%) and the desired product (0.12 g, 34%).

$^1$H NMR (500 MHz, DMSO): δ 8.28 (1H, s, H-8), 7.78 (2H, br s, NH$_2$), 6.26 (1H, t, J=6.6 Hz, H-1'), 5.39 (1H, br s, 3'-OH), 4.40 (1H, m, H-3'), 3.87 (1H, m, H-4'), 3.84-3.68 (2H, m, 2×H-5'), 2.69, 2.33 (2H, 2×m, 2×H-2') 0.85 (9H, s, C(CH$_3$)$_3$), 0.02 (6H, s, Si(CH$_3$)$_2$).

Standard Procedure A

Protected nucleoside A (78 mg, 0.20 mmol) was dissolved in anhydrous tetrahydrofuran under argon and 1M tBuMgCl in THF (0.4 mL, 0.4 mmol) was added dropwise followed by slow addition of the desired phosphorochloridate (0.4 mmol) in anhydrous THF. The mixture was stirred at room temperature overnight. The solvent was evaporated and the residue was purified by silica gel column chromatography with 3% MeOH in DCM as an eluent. The obtained compound was dissolved in H$_2$O/THF (1:1) and TFA was added dropwise. The mixture was stirred at room temperature for 30 min and NaHCO$_3$ added to neutralise the solution. The solvents were evaporated and the residue purified by silica gel column chromatography and preparative thin layer chromatography (TLC) (10% MeOH in DCM).

2-Chloro-2'-deoxyadenosine-3'-[phenyl-(ethoxy-L-alaninyl)]-phosphate 1

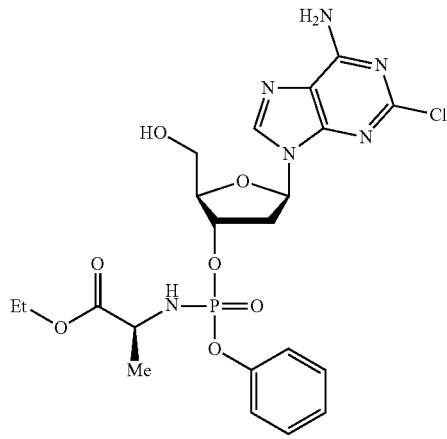

Prepared according to a Standard Procedure A, using 5'-protected cladribine A (0.1 g, 0.17 mmol) in anhydrous THF, tBuMgCl (1M solution THF, 0.34 mL, 0.34 mmol), phenyl-(ethoxy-L-alaninyl)-phosphorochloridate (0.10 g, 0.34 mmol). After deprotection with TFA the crude mixture was purified by column chromatography (4% MeOH in DCM) followed by preparative TLC (4% MeOH in DCM) to give the pure product as a white solid (19.0 mg, 21%). $^{31}$P-NMR (202 MHz, CD$_3$OD): δ 3.28, 2.76. $^1$H-NMR (500 MHz, CD$_3$OD): δ 8.32, 8.28 (1H, 2×s, H-8), 7.41-7.22 (5H, m, H—Ar), 6.43, 6.33 (1H, 2×t, J=7.0 Hz, H-1'), 5.3, 5.29 (1H, 2×br s, H-3'), 4.32, 4.31 (1H, 2×br s, H-4'), 4.22-4.15 (2H, m, CH$_2$CH$_3$), 4.05-4.00 (1H, m, NHCHCH$_3$), 3.86-3.80 (2H, m, 2×H-5'), 3.01-2.90 (1H, m, H-2'$_a$), 2.81-2.78 (0.5H, m, H-2'$_b$ one diastereoisomer), 2.68-2.64 (0.5H, m, H-2'$_b$ one diastereoisomer), 1.42-1.36 (3H, 2×d, J=7.0 Hz, NHCHCH$_3$), 1.30-1.24 (3H, m, CH$_2$CH$_3$). MS (ES+) m/z: 563.1 (M+Na$^+$, 100%); Accurate mass: C$_{21}$H$_{26}$ClN$_6$O$_7$NaP required m/z 563.1187, found m/z 563.1183. Reverse-phase HPLC eluting with H$_2$O/CH$_3$CN from 100/0 to 0/100 in 20 min, flow=1 ml/min, A=254, t$_R$=12.31, 12.41 min.

2-Chloro-2'-deoxyadenosine-3'-[phenyl-(tert-butoxy-L-alaninyl)]-phosphate 2

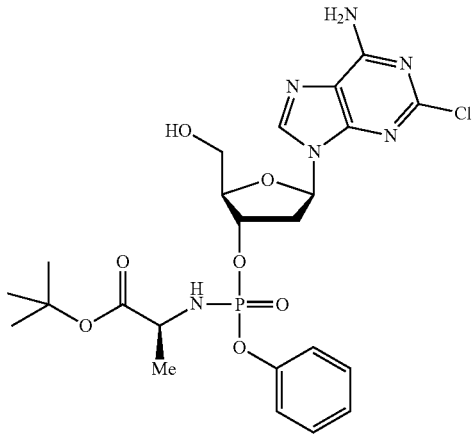

Prepared according to Standard Procedure A, using 5'-protected cladribine A (0.10 g, 0.17 mmol) in dry THF, tBuMgCl (1M solution THF, 0.34 mL, 0.34 mmol), phenyl-(tert-butoxy-L-alaninyl)-phosphorochloridate (0.11 g, 0.34 mmol). After deprotection with TFA the crude was purified by column chromatography (4% MeOH in DCM) to give the pure product as a white solid (43.8 mg, 45%). $^{31}$P-NMR (202 MHz, CD$_3$OD): δ 3.30, 2.91; $^1$H-NMR (500 MHz, CD$_3$OD): δ 8.31, 8.27 (1H, 2×s, H-8), 7.42-7.21 (5H, m, H—Ar), 6.43, 6.34 (1H, 2×t, J=7.0 Hz, H-1'), 5.36, 5.30 (1H, 2×br s, H-3'), 4.35, 4.30 (1H, 2×br s, H-4'), 3.91-3.80 (3H, m, NHCHCH$_3$, 2×H-5'), 3.02-2.90 (1H, m, H-2'$_a$), 2.81-2.77 (0.5H, m, H-2'$_b$ one diastereoisomer), 2.68-2.65 (0.5H, m, H-2'$_b$ one diastereoisomer), 1.49, 1.46 (9H, 2×s, C(CH$_3$)$_3$), 1.38, 1.34 (3H, 2×d, J=7.0 Hz, NHCHCH$_3$). MS (ES+) m/z: 591.1 (M+Na$^+$, 100%); Accurate mass: C$_{23}$H$_{30}$ClN$_6$O$_7$NaP required m/z 591.1500, m/z found 591.1509. Reverse-phase HPLC eluting with H$_2$O/CH$_3$CN from 100/0 to 0/100 in 20 min, flow=1 ml/min, A=254, t$_R$=15.24, 15.36 min.

2-Chloro-2'-deoxyadenosine-3'-[phenyl-(benzoxy-D-alaninyl)]-phosphate 3

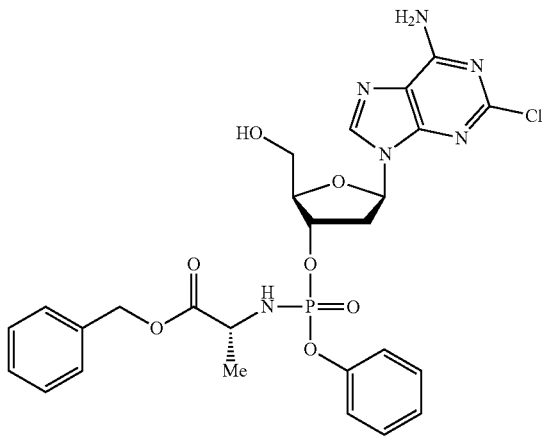

Prepared according to Standard Procedure A, using 5'-protected cladribine A (0.11 g, 0.19 mmol) in anhydrous THF, tBuMgCl (1M solution THF, 0.37 mL, 0.37 mmol), phenyl-(benzoxy-D-alaninyl-phosphorochloridate (0.13 g, 0.37 mmol). After deprotection with TFA the crude was purified by column chromatography (4% MeOH in DCM) to give the pure product as a white solid (40.0 mg, 35%). $^{31}$P-NMR (202 MHz, CD$_3$OD): δ 3.06, 2.77. $^1$H-NMR (500 MHz, CD$_3$OD): δ 8.24, 8.22 (1H, 2×s, H-8), 7.39-7.16 (10H, m, H—Ar), 6.32-6.26 (1H, m, H-1'), 5.34-5.32, 5.23-5.21 (1H, 2×m, H-3'), 5.19-5.14 (2H, m, CH$_2$Ph), 4.36-4.34 (0.5H, m, H-4' one diastereoisomer), 4.22-4.20 (0.5H, m, H-4' one diastereoisomer) 4.10-4.04 (1H, m, NHCHCH$_3$), 3.85-3.72 (2H, m, 2×H-5'), 2.87-2.82, 2.77-2.67 (1H, 2×m, H-2'$_a$), 2.59, 2.48 (1H, 2×ddd, J=14.0, 5.8, 1.9 Hz, H-2'$_b$), 1.41, 1.38 (3H, 2×dd, J=7.0, 4.5 Hz, NHCHCH$_3$). MS (ES+) m/z: 625.1 (M+Na$^+$, 100%); Accurate mass: C$_{26}$H$_{28}$ClN$_6$O$_7$NaP required m/z 625.1343, found m/z 625.1351. Reverse-phase HPLC eluting with H$_2$O/CH$_3$CN from 100/0 to 0/100 in 20 min, flow=1 ml/min, A=254, $t_R$=14.16 min.

2-Chloro-2'-deoxyadenosine-3'-[phenyl-(benzoxy-glycinyl)]-phosphate 4

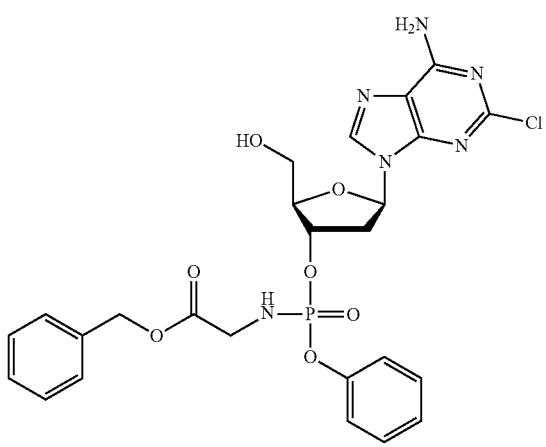

Prepared according to Standard Procedure A, using 5'-protected cladribine A (0.12 g, 0.20 mmol) in anhydrous THF, tBuMgCl (1M solution THF, 0.40 mL, 0.40 mmol), phenyl-(benzoxy-L-glycinyl)-phosphorochloridate (0.14 g, 0.40 mmol). After deprotection with TFA the crude was purified by column chromatography (4% MeOH in DCM) to give the pure product as a white foamy solid (15.0 mg, 13%). $^{31}$P-NMR (202 MHz, CD$_3$OD): δ 4.21, 4.05. $^1$H-NMR (500 MHz, CD$_3$OD): δ 8.14, 8.13 (1H, 2×s, H-8), 7.29-7.08 (10H, m, H—Ar), 6.23-6.16 (1H, m, H-1'), 5.24-5.21 (1H, m, H-3'), 5.08-5.06 (2H, m, CH$_2$Ph), 4.20-4.19 (0.5H, m, H-4' one diastereoisomer), 4.14-4.12 (0.5H, m, H-4' one diastereoisomer), 3.77-3.63 (4H, m, NHCH$_2$, 2×H-5'), 2.76-2.70 (1H, m, H-2'), 2.51-2.47 (1H, m, H-2'). MS (ES+) m/z: 611.1 (M+Na$^+$, 100%); Accurate mass: C$_{25}$H$_{26}$ClN$_6$O$_7$NaP required m/z 611.1187, found m/z 611.1180. Reverse-phase HPLC eluting with H$_2$O/CH$_3$CN from 100/0 to 0/100 in 20 min, flow=1 ml/min, λ=254, $t_R$=13.64 min.

Further compounds of the invention can be made according to Standard Procedure A analogously to compounds 1 to 4. Examples include the following compounds:

2-Chloro-2'-deoxyadenosine-3'-[phenyl-(benzoxy-L-leucinyl)]-phosphate 5

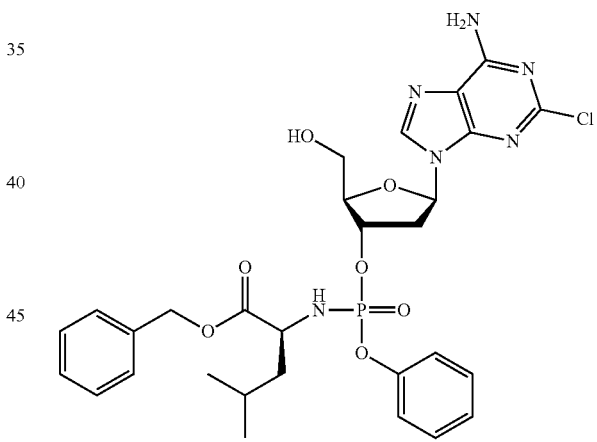

$^{31}$P-NMR (CD$_3$OD, 202 MHz): δ 3.58, 2.81; $^1$H-NMR (CD$_3$OD, 500 MHz): δ 8.28, 8.23 (1H, 2×s, H-8), 7.40-7.22 (10H, m, H—Ar), 6.36, 6.25 (1H, 2×t, J=7.0 Hz, H-1'), 5.30, 5.24 (1H, 2×br s, H-3'), 5.19-5.14 (2H, m, CH$_2$Ph), 4.25 (1H, br s, H-4'), 3.98-3.95 (1H, m, NHCH), 3.84-3.73 (2H, m, 2×H-5'), 2.89-2.55 (2H, m, 2×H-2'), 1.77-1.72 (1H, m, CH(CH$_3$)$_2$), 1.60-1.56 (2H, m, CH$_2$CH(CH$_3$)$_2$), 0.94-0.88 (6H, m, CH(CH$_3$)$_2$). MS (ES+) m/z: 667.2 (M+Na$^+$, 100%); Accurate mass: C$_{29}$H$_{34}$ClN$_6$O$_7$NaP required m/z 667.1813, found m/z 667.1799. Reverse-phase HPLC eluting with H$_2$O/CH$_3$CN from 100/0 to 0/100 in 20 min, flow=1 ml/min, A=254, $t_R$=16.27, 16.47 min.

2-Chloro-2'-deoxyadenosine-3'-[1-naphthyl-(2,2-dimethylpropoxy-L-alaninyl)]phosphate 6

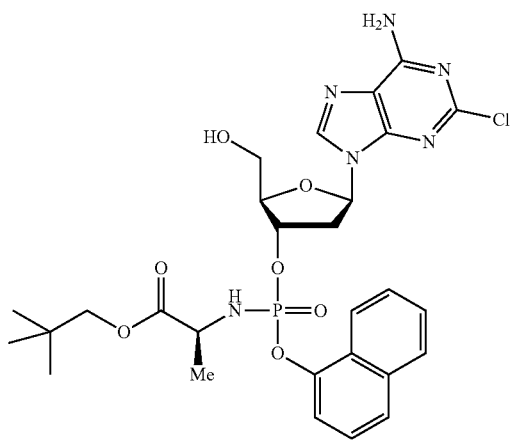

$^{31}$P-NMR (202 MHz, CD$_3$OD): δ 3.68, 3.27. $^1$H-NMR (500 MHz, CD$_3$OD): δ 8.28-8.20 (2H, m, H-8, H—Ar), 7.92 (1H, d, J=8.0 Hz, H—Ar), 7.75 (1H, d, J=8.2 Hz, H—Ar), 7.63-7.47 (4H, m, H—Ar), 6.38-6.21 (1H, 2×m, H-1'), 5.39-5.33 (1H, 2×m, H-3'), 4.32-4.23 (1H, 2×m, H-4'), 4.17-4.11 (1H, m, NHCHCH$_3$), 3.89-3.71 (4H, m, 2×H-5', CH$_2$C(CH$_3$)$_3$), 2.96-2.78, 2.58-2.55 (2H, 2×m, 2×H-2'), 1.43, 1.38 (3H, 2×d, J=7.25 Hz, NHCHCH$_3$), 0.95, 0.93 (2×s, 9H, CH$_2$C(CH$_3$)$_3$). MS (ES+) m/z: 656 (M+Na$^+$), 634 (M+H$^+$); C$_{28}$H$_{34}$ClN$_6$O$_7$P mass required 633.03.

2-Chloro-2'-deoxyadenosine-3'-[1-naphthyl-(pentoxy-L-leucinyl)] phosphate 7

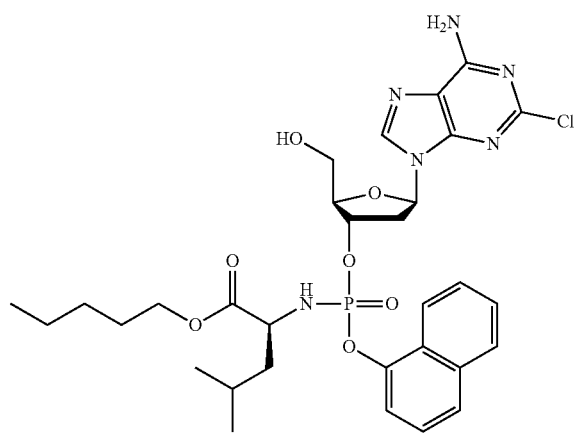

$^{31}$P-NMR (202 MHz, CD$_3$OD): δ 4.02, 3.48. $^1$H-NMR (500 MHz, CD$_3$OD): δ 8.24, 8.21 (1H, 2×s, H-8), 7.94, 7.92 (1H, 2×s, H—Ar), 7.76, 7.53 (1H, 2×s, H—Ar), 7.63-7.55 (4H, m, H—Ar), 7.52, 7.47 (1H, 2×s, H—Ar), 6.40-6.33, 6.23-6.20 (1H, 2×m, H-1'), 5.40-5.38, 5.32-5.29 (1H, 2×m, H-3'), 4.34-4.33, 4.26-4.24 (1H, 2×m, H-4'), 4.08-4.05 (2H, m, 2×H-5'), 4.01-3.97 (1H, m, NHCHCH$_2$CH(CH$_3$)$_2$), 3.88-3.80 (2H, m, NHCHCH$_2$CH(CH$_3$)$_2$), 3.00-2.95, 2.89-2.79, 2.58-2.54 (2H, 3×m, 2×H-2'), 1.75-1.69 (1H, m, NHCHCH$_2$CH(CH$_3$)$_2$), 1.63-1.55 (4H, m, 2×CH$_2$, OCH$_2$CH$_2$CH$_2$CH$_2$CH$_3$), 1.35-1.28 (4H, m, 2×CH$_2$, OCH$_2$CH$_2$CH$_2$CH$_2$CH$_3$), 0.91-0.82 (9H, m, OCH$_2$CH$_2$CH$_2$CH$_2$CH$_3$, NHCHCH$_2$CH(CH$_3$)$_2$). MS (ES$^+$) m/z: 697 (M+Na$^+$), 675 (M+H$^+$), C$_{31}$H$_{40}$ClN$_6$O$_7$P mass required 674.24.

2-Chloro-2'-deoxyadenosine-3'-[1-naphthyl-(cyclohexoxy-L-alaninyl)] phosphate 8

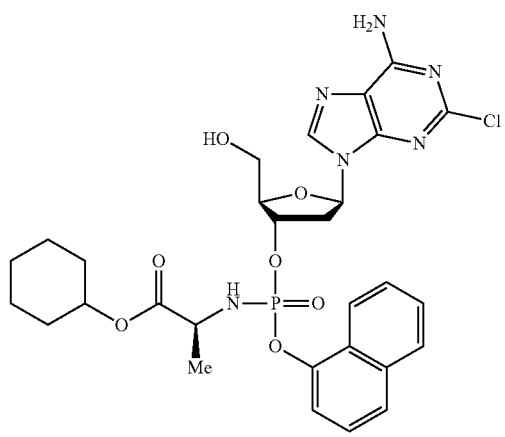

$^{31}$P-NMR (202 MHz, CD$_3$OD) δ 3.34, 2.80. $^1$H-NMR (500 MHz, CD$_3$OD): δ 8.33-8.28 (2H, m, H-8, H—Ar), 7.85-7.81 (1H, m, H—Ar), 7.62-7.59 (1H, m, H—Ar), 7.56-7.52 (3H, m, H—Ar), 7.47-7.43 (1H, m, H—Ar), 6.30 (1H, t, J=6.5 Hz, H-1'), 4.66-4.57 (3H, m, H-3', OCH-ester), 4.51-4.48 (2H, m, 2×H-5'), 4.20-4.18 (1H, m, H-4'), 4.12-3.96 (1H, m, NHCHCH$_3$), 2.67-2.54 (1H, m, H-2'), 2.50-2.46 (1H, m, H-2'), 1.75-1.71 (4H, m, 2×CH$_2$-ester), 1.32-1.30 (9H, m, 3×CH$_2$-ester, NHCHCH$_3$). MS (ES$^+$) m/z: 667 (M+Na$^+$), 645 (M+H+); C$_{29}$H$_{34}$ClN$_6$O$_7$P mass required 644.19.

2-Chloro-2'-deoxyadenosine-3'-[phenyl-(cyclohexoxy-L-alaninyl)] phosphate 9

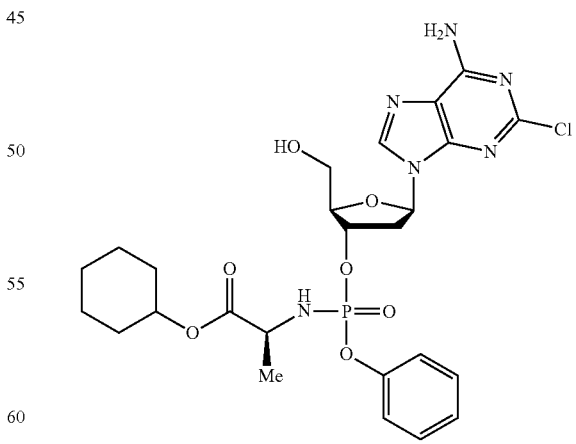

$^{31}$P-NMR (202 MHz, CD$_3$OD): δ 3.34, 2.80. $^1$H-NMR (500 MHz, CD$_3$OD): δ 8.32-8.28 (1H, m, H-8), 7.43-7.37 (2H, m, H—Ar), 7.31-7.22 (3H, m, H—Ar), 6.44-6.41, 6.36-6.29 (1H, 2×m, H-1'), 5.37-5.34, 5.30-5.27 (1H, 2×m, H-3'), 4.81-4.74 (1H, m, CH-ester), 4.33-4.25 (1H, m, H-4'), 4.01-3.92 (1H, m, NHCHCH₃), 3.87-3.79 (2H, m, 2×H-5'), 3.01-2.89 (1H, m, H-2'), 2.82-2.77, 2.67-2.63 (1H, 2×m, H-2'), 1.86-1.74 (4H, m, 2×CH₂-ester), 1.57-1.30 (9H, m, 3×CH₂-ester, NHCHCH₃). MS (ES+) m/z: 617 (M+Na⁺), 595 (M+H+); C₂₅H₃₂ClN₆O₇P mass required 594.18.

2-Chloro-2'-deoxyadenosine-3'-[phenyl-(2,2-dimethylpropoxy-L-alaninyl)] phosphate 10

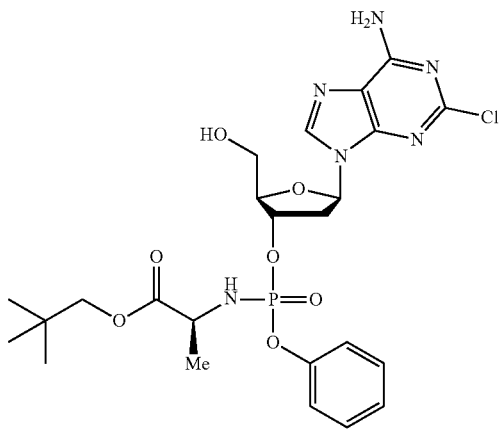

³¹P-NMR (202 MHz, CD₃OD): δ 3.30, 2.76. ¹H-NMR (500 MHz, CD₃OD): δ 8.32, 8.27, 8.23, 8.07 (1H, 4×s, H-8), 7.57-7.52, 7.43-7.38, 7.31-7.22 (5H, 3×m, H—Ar), 6.44-6.41, 6.36-6.30 (1H, 2×m, H-1'), 5.38-5.36, 5.30-5.27 (1H, 2×m, H-3'), 4.32 4.30, 4.27-4.25 (1H, 2×m, H-4'), 4.15-4.12, 4.08-4.04 (1H, 2×m, NHCHCH₃), 3.87 3.79 (1H, m, H-5'), 3.92-3.80 (2H, m, CH₂C(CH₃)₃), 3.68, 3.58 (1H, 2×dd, J=12.0, 5.0 Hz, H-5'), 3.01-2.89, 2.81-2.64, 2.35-2.29 (2H, 3×m, 2×H-2'), 1.44, 1.39 (3H, 2×d, J=7.5 Hz, NHCHCH₃), 0.98, 0.96 (9H, 2×s, CH₂C(CH₃)₃). MS (ES+) m/z: 605 (M+Na⁺), 583 (M+H⁺), C₂₄H₃₂ClN₆O₇P mass required 582.18.

2-Chloro-2'-deoxyadenosine-3'-[phenyl-(ethoxy-2,2-dimethylglycinyl)]-phosphate 11

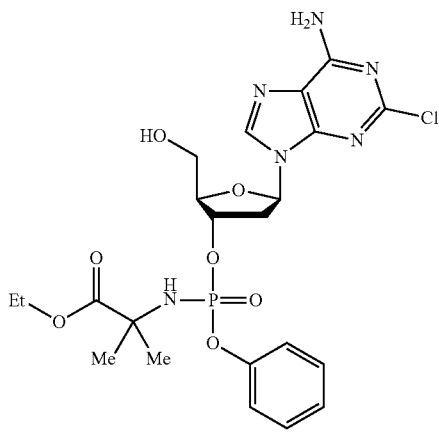

³¹P-NMR (202 MHz, CD₃OD): δ 1.60, 1.55. ¹H-NMR (500 MHz, CD₃OD): δ 8.32, 8.28 (1H, 2×s, H-8), 7.45-7.38, 7.33-7.27, 7.24-7.21 (5H, 3×m, H—Ar), 6.41, 6.33 (1H, 2×dd, J=8.1, 5.8 Hz, H-1'), 5.36-5.32 (1H, m, H-3'), 4.39, 4.29 (1H, 2×m, H-4'), 4.20, 4.19 (2H, 2×q, J=7.2 Hz, CH₂CH₃), 3.92-3.76 (2H, m, 2×H-5'), 3.00-2.88, 2.78-2.63 (2H, 3×m, 2×H-2'), 1.53 (6H, br s, (CH₃)₂), 1.29, 1.28 (3H, 2×t, J=7.1 Hz, CH₂CH₃). MS (ES⁺) m/z: 577.7 (M+Na⁺), C₂₂H₂₈ClN₆O₇P mass required 554.92

2-Chloro-2'-deoxyadenosine-3'-[phenyl-(benzoxy-L-phenylalaninyl)] phosphate 12

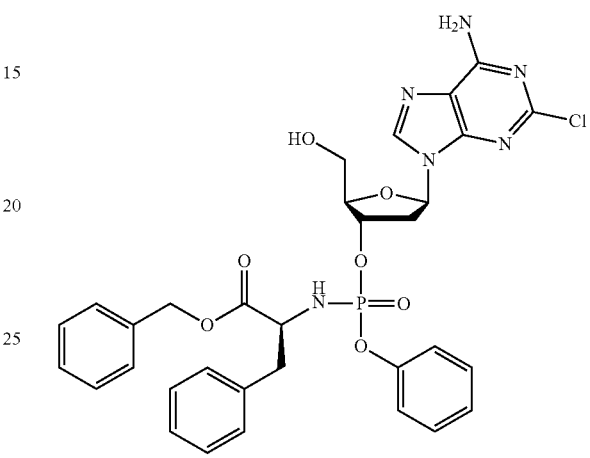

³¹P-NMR (202 MHz, CDCl₃): δ 1.42, 1.23. ¹H-NMR (500 MHz, CDCl₃): δ 7.69, 7.55 (1H, 2×s, H-8), 7.28-6.92 (15H, m, H—Ar), 6.11 (2H, br s, NH₂), 6.01-5.86 (1H, m, H-1'), 5.30-5.02 (4H, m, H-3', OH-3', OCH₂Ph), 4.31-4.15 (2H, m, H-4', NHCHCH₂Ph), 3.86-3.65 (3H, m, 2×H-5', NHCHCH₂Ph), 2.98-2.81 (3H, m, NHCHCH₂Ph, H-2ₐ'), 2.39-2.31 (1H, m, H-2b'). MS (ES⁺) m/z: 679 [M+H⁺], 681 [M(³⁷Cl)+H⁺], 701 [M+Na⁺], 703 [M(³⁷Cl)+Na⁺], 717 [M+K+], 719 [M(³⁷Cl)+K+]; C₃₂H₃₂ClN₆O₇P mass required m/z 678.18. Reverse-phase HPLC eluting with H₂O/CH₃CN from 100/0 to 0/100 in 10 min, flow=1 ml/min, λ=254, t_R=9.19 min.

2-Chloro-2'-deoxyadenosine-3'-[1-naphthyl(benzoxy-L-phenylaninyl)] phosphate 13

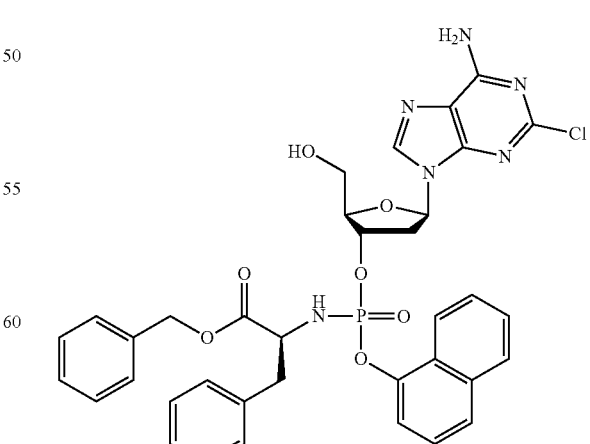

31P-NMR (202 MHz, CDCl3): δ 2.09, 1.78. 1H-NMR (500 MHz, CDCl3): δ 8.02-7.91 (1H, m, H-8), 7.81-7.79 (1H, m, H—Ar), 7.65-7.60 (1H, m, H—Ar), 7.49-7.41 (4H, m, H—Ar), 7.33-6.75 (11H, m, H-3 Naph, OCH2Ph, CHCH2Ph), 6.00 (2H, br s, NH2), 5.92-5.62 (1H, 2m, H-1'), 5.28-5.13 (2H, m, H-3' OH-3'), 5.05-4.89 (2H, m, OCH2Ph), 4.34-4.27 (1H, m, NHCHCH2Ph), 4.18-4.12 (1H, 2m, H-4') 3.83-3.61 (3H, m, 2×H-5', NHCHCH2Ph), 2.95-2.88 (2H, m, NHCHCH2Ph), 2.84-2.79 (1H, m, H-2'$_a$), 2.30-2.14 (1H, m, H-2'$_b$). MS (ES+) m/z: 729 [M+H+], 751 [M+Na+], 767 [M+K+]; Accurate mass: C36H34ClN6O7P required m/z 728.19. Reverse phase HPLC from H2O/CH3CN from 100/0 to 0/100 in 10 min, flow=1 ml/min, λ=254, $t_R$=10.33 min.

2-Chloro-2'-deoxyadenosine-3'-[phenyl-(benzoxy-L-valinyl)] phosphate 14

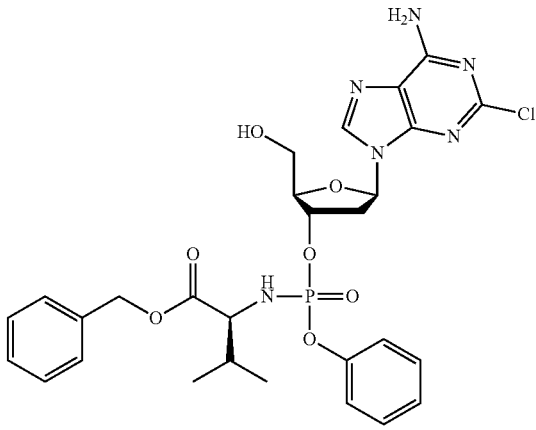

31P-NMR (202 MHz, CDCl3): δ 2.40, 2.20. 1H-NMR (500 MHz, CDCl3): δ 7.74, 7.58 (1H, 2×s, H-8), 7.30-7.09 (10H, m, H—Ar), 6.13-6.11, 6.27-6.24 (1H, 2×m, H-1'), 5.91 (2H, br s, NH2), 5.27-5.25 (1H, m, H-3'), 5.10-5.04 (2H, m, CH2Ph), 4.25-4.21 (1H, m, H-4'), 3.86-3.62 (4H, m, 2×H-5', NHCHCH(CH3)2, NHCHCH(CH3)2), 2.95-2.90 (1H, m, 2.45-2.37 (1H, m, H-2'$_b$), 2.02-1.99 (1H, m, NHCHCH(CH3)2), 0.88-0.77 (6H, m, NHCHCH(CH3)2). MS (ES+) m/z: 632 [M+H+], 655 [M+Na+]. C28H32ClN6O7P mass required m/z 631.18.

2-Chloro-2'-deoxyadenosine-3'-[phenylaso-propoxy-L-alaninyl)] phosphate 15

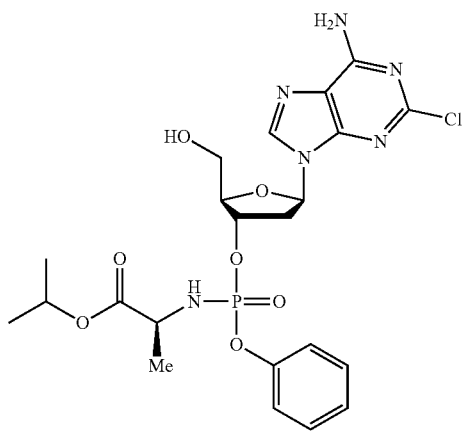

31P-NMR (202 MHz, CDCl3): δ 1.54, 1.34. 1H-NMR (500 MHz, CDCl3): δ 7.79, 7.71 (1H, 2s, H-8), 7.31-7.12 (5H, m, H—Ar), 6.21-6.17, 6.05-6.01 (1H, 2×m, H-1'), 5.70 (2H, br s, NH2), 5.31-5.26 (1H, m, H-3'), 4.99-4.93 (1H, m, OCH(CH3)2), 4.44-4.42 (1H, m, H-4'), 3.98-3.87 (2H, m, NHCHCH3, OH-5'), 3.82-3.74 (1H, m, NHCHCH3), 3.67-3.53 (3H, m, 2×H-5', NHCHCH3), 3.08-2.97 (1H, m, H-2'), 2.62-2.49 (1H, m, H-2'), 1.34, 1.30 (3H, 2×d, J=7.0 Hz, NHCHCH3), 1.22-1.19 (6H, m, OCH(CH3)2). MS (ES+) m/z: 555 [M+H+], 556 [M(13C)+H+], 557 [M(37Cl)+H], 558 [M(37Cl, 13C)+H+], 577 [M+Na+], 578 [M(13C)+Na+], 579 [M(37Cl)+Na+], 580 [M(37Cl, 13C)+]. C22H28ClN6O7P mass required m/z 554.14. Reverse-phase HPLC eluting with H2O/CH3CN from 100/0 to 0/100 in 15 min, flow=1 ml/min, A=254, $t_R$=9.92 min.

2-Chloro-2'-deoxyadenosine-3'-[phenyl-(2-butoxy-L-alaninyl)] phosphate 16

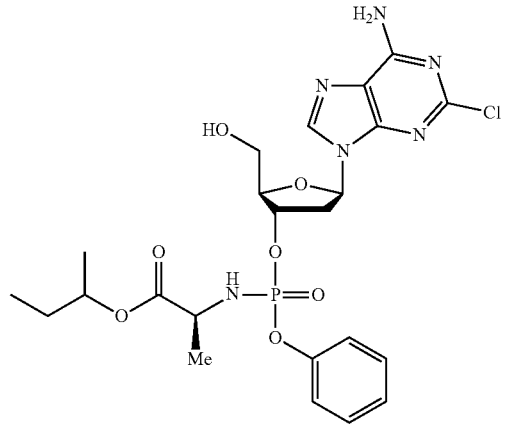

31P-NMR (202 MHz, CDCl3): δ 1.62, 1.60. 1H-NMR (500 MHz, CDCl3): δ 7.81, 7.73 (1H, 2×s, H-8), 7.30-7.11 (5H, m, H—Ar), 6.21-6.03 (3H, m, H-1', NH2), 5.32-5.23 (2H, m, H-3', NHCHCH3), 4.85-4.76 (1H, m, OCH(CH3)CH2CH3), 4.34-4.31 (1H, m, H-4'), 3.95-3.75 (4H, m, NHCHCH3, 2×H-5', OH-5'), 3.07-2.95 (1H, m, H-2$_a$'), 2.48-2.26 (1H, m, H-2b'), 1.55-1.47 (2H, m, OCH(CH3)CH2CH3), 1.37-1.31 (3H, m, NHCHCH3), 1.19-1.09 (3H, m, OCH(CH3)CH2CH3), 0.85-0.79 (3H, m, OCH(CH3)CH2CH3). MS (ES+) m/z: 569 [M+H+], 570 [M(13C)+H+], 571 [M(37Cl)+H+], 572 [M(37Cl, 13C)+H+], 591 [M+Na+], 592 [M(13C)+Na+], 593 [M(37Cl)+Na+], 594 [M(37Cl, 13C)+Na+], 607 [M+K+], 608 [M(13C)+K+], 609 [M(37Cl)+K+]. C23H30ClN6O7P mass required m/z 568. Reverse-phase HPLC eluting with H2O/CH3CN from 100/0 to 0/100 in 15 min, flow=1 ml/min, Δ=254, $t_R$=10.48 min.

2-Chloro-2'-deoxyadenosine-3'-[phenyl-((S)-1-phenylethoxy-L-alaninyl)-phosphate 17

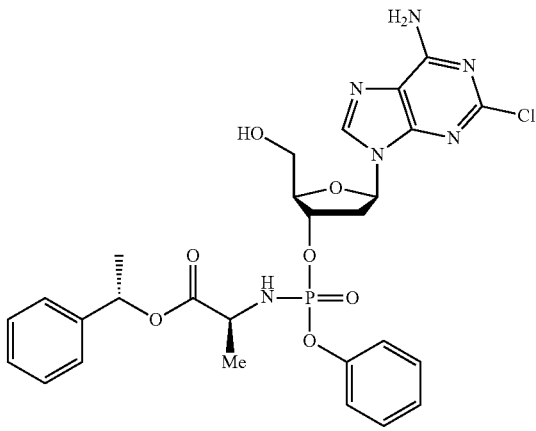

$^{31}$P-NMR (202 MHz, CDCl$_3$): δ 3.34, 2.65. $^1$H-NMR (500 MHz, CDCl$_3$): δ 8.20 (1H, m, H-8), 7.47-7.28 (8H, m, H—Ar), 7.27-7.15 (2H, m, H—Ar), 6.40-6.33, 6.32-6.26, (1H, 2×m, H-1'), 5.96-5.84 (1H, m, CHCH$_3$Ph), 5.35-5.21 (1H, m, H-3'), 4.40-4.26 (1H, m, H-4'), 4.10-4.02 (1H, m, NHCHCH$_3$), 3.87-3.74 (2H, m, 2×H-5'), 2.94-2.83 (1H, m, 2.74-2.57 (1H, m, H-2b'), 1.60-1.48 (3H, m, CHCH$_3$Ph), 1.43-1.20 (3H, m, NHCHCH$_3$). MS (ES+) m/z: 639 [M+Na$^+$], 640 [M($^{37}$Cl)+Na$^+$]. C$_{27}$H$_{30}$ClN$_6$O$_7$PNa mass required m/z 639.99. Reverse-phase HPLC eluting with H$_2$O/MeOH from 100/0 to 0/100 in 35 min, flow=1 ml/min, A=254, $t_R$=29.19, 29.54 min.

2-Chloro-2'-deoxyadenosine-3'-[1-naphthyl-(benzoxy-L-alaninyl)-phosphate 18

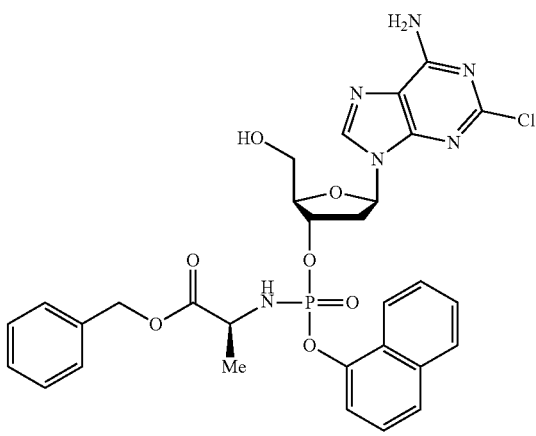

Protected nucleoside A (78 mg, 0.20 mmol) was dissolved in anhydrous THF (7 mL) under argon and tBuMgCl (1.0 M in THF, 1.0 mL, 1.0 mmol) was added dropwise followed by slow addition of 1-naphthyl-(benzoxy-L-alaninyl)-phosphorochloridate (0.40 g, 0.99 mmol) in anhydrous THF (2.0 mL). The mixture was stirred at room temperature overnight. The solvent was evaporated at the residue purified by silica gel column chromatography (3% MeOH in DCM). The obtained compound was dissolved in H$_2$O/THF (4 mL+4 mL) and TFA (1 mL) was added dropwise. The mixture was stirred at room temperature for 30 min and NaHCO$_3$ added to neutralise the solution. The solvents were evaporated and the residue purified by silica gel column chromatography (0-4% MeOH in DCM) and preparative TLC (10% MeOH in DCM). Yield: 50 mg. 38% over 2 steps. $^{31}$P-NMR (202 MHz, CD$_3$OD): δ 3.71, 3.10. $^1$H-NMR (500 MHz, CD$_3$OD): δ 8.17, 8.14 (2H, 2×s, H-8, H—Ar), 7.88 (1H, d, J=7.7 Hz, H—Ar), 7.71 (1H, dd, J=8.1, 4.2 Hz, H—Ar), 7.59-7.41 (4H, m, H—Ar), 7.35-7.16 (5H, m, H—Ar), 6.30, 6.15 (1H, 2×dd, J=8.4, 5.9 Hz, H-1'), 5.33 (1H, m, H-3'), 5.18-5.06 (2H, m, CH$_2$Ph), 4.27-4.24, 4.21-4.12 (2H, 2×m, H-4', NHCHCH$_3$), 3.84-3.67 (2H, m, 2×H-5'), 2.82-2.78 (1H, m, H-2$_a$'), 2.69-2.65, 2.64-2.61 (1H, 2×m, H-2b'), 1.40, 1.35 (3H, 2×d, J=7.2 Hz, NHCHCH$_3$). MS (ES$^+$) m/z: 676.16 (M+Na$^+$). C$_{30}$H$_{30}$ClN$_6$O$_7$PNa mass required m/z 676.02. Reverse-phase HPLC eluting with H$_2$O/MeOH from 100/0 to 0/100 in 40 min, flow=1 ml/min, λ=254, $t_R$=20.6, 21.1 min.

2-Chloro-2'-deoxyadenosine-3'-[phenyl-(benzoxy-L-alaninyl)-phosphate 19

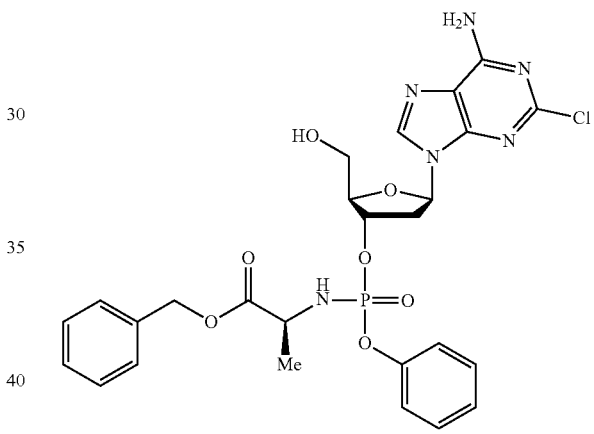

Protected nucleoside A (0.12 g, 0.30 mmol) was dissolved in anhydrous THF (10 mL) under argon and tBuMgCl (1.0 M in THF, 1.5 mL=1.5 mmol) was added dropwise. Phenyl-(benzoxy-L-alaninyl)-phosphorochloridate (0.53 g, 1.50 mmol) in anhydrous THF (2 mL) was added slowly and the mixture was stirred at room temperature overnight. The solvent was evaporated and the residue purified by silica gel column chromatography (4% MeOH in DCM). The obtained compound was dissolved in H$_2$O/THF (4 mL+1 mL) and TFA (1 mL) was added dropwise. The mixture was stirred at room temperature for 45 min before NaHCO$_3$ was added to neutralise the solution. Silica gel column chromatography gave the desired product. Yield: 37 mg, 20% over 2 steps. $^{31}$P-NMR (202 MHz, CD$_3$OD): δ 3.3, 2.6. $^1$H-NMR (500 MHz, CD$_3$OD): δ 8.26, 8.21 (1H, 2×s, H-8), 7.41-7.18 (10H, m, H—Ar), 6.36, 6.26 (1H, 2×dd J=8.4, 5.8 Hz, H-1'), 5.31-5.28, 5.27-5.24 (1H, 2×m, H-3'), 5.19, 5.15 (2H, 2×s, CH$_2$Ph), 4.26-4.21 (1H, m, H-4'), 3.85-3.74 (2H, m, 2×H-5'), 2.85-2.81, 2.69-2.62, 2.60-2.57 (2H, 3×m, H-2'), 1.41, 1.37 (3H, 2×dd, J=7.2, 1.2 Hz, NHCHCH$_3$). MS (ES$^+$) m/z: 626.11 (M+Na$^+$). C$_{26}$H$_{28}$ClN$_6$O$_7$PNa mass required m/z 626.14. Reverse-phase HPLC eluting with H$_2$O/MeOH from 100/0 to 0/100 in 35 min, flow=1 ml/min, λ=254, $t_R$=18.9, 19.6 min.

Anticancer Activity

The compounds of the invention have been compared to cladribine and to compound Y, a 5'-phosphoramidate of cladribine.

The cell lines used include:
HEL92.1.7: erythroleukaemia
HL-60: promyelocytic leukaemia
KG-1: acute myelogenous leukaemia
K562: chronic myelogenous leukaemia
L1210: lymphoblast cell line derived from a mouse with lymphocytic leukaemia
MCF7: human mammary epithelial adenocarcinoma (oestrogen sensitive) cell line
NB4: all-trans retinoic acid sensitive acute promyelocytic leukemia
NB4R2: all-trans retinoic acid insensitive acute promyelocytic leukemia
RL: non-Hodgkin's lymphoma
U937: histiocytic lymphoma
Z-138: mantle cell lymphoma Example 1: In Vitro Cytotoxicity Studies Cladribine phosphoramidate derivatives were evaluated against six leukaemic cell lines (KG1, U937, K562, NB4R2, NB4 and HL-60) in vitro. Inhibitory concentration ($IC_{50}$) at which 50% of the cells were no longer viable (calculated using MTS assay) was determined. Cells were treated with Cladribine and its 3'-phosphoramidate derivatives at concentrations between 100 µM and 0.02 µM by serial dilutions and incubated for 72 h at 37° C., 5% $CO_2$ in a final volume of 90 µL. Twenty microliters of MTS reagent (Promega UK Ltd, Southampton, Hants) was added to the tumour cell cultures and reaction incubated for a further 4 h at 37° C., 5% $CO_2$. The absorbance of the reaction after this time was read by spectrophotometry at 490 nm and the percentage of viable cells calculated relative to untreated control cells in the same assay.

Table 1 shows the in vitro results for compounds of the invention against the leukaemic cell lines KG1, U937, K562, NB4R2, NB4 and HL-60.

| Compound | KG1 µM | U937 µM | K562 µM | NB4R2 µM | NB4 µM | HL-60 µM |
| --- | --- | --- | --- | --- | --- | --- |
| Cladribine | 0.06 | 0.02 | 0.53 | 0.06 | 0.04 | 0.09 |
| Y | 0.67 | 0.08 | 8.05 | 0.63 | 0.23 | 1.75 |
| 19 | 0.38 | 0.03 | >10 | 0.11 | 0.24 | 0.10 |
| 18 | 0.31 | 0.01 | 5.14 | 1.29 | 0.07 | 0.39 |
| 1 | 1.76 | 3.06 | >10 | 2.52 | 0.74 | 2.68 |
| 15 | 5.0 | 0.4 | >10 | 9.0 | 6.0 | 2.0 |
| 2 | 2.0 | 6.0 | >10 | >10 | >10 | >10 |
| 10 | — | — | — | — | >10 | 5.3 |
| 6 | — | — | — | — | 1.0 | 0.3 |
| 16 | 7.0 | 2.0 | >10 | >10 | 9.0 | 8.0 |
| 17 | — | — | — | — | 5.5 | 3.2 |
| 3 | >10 | 7.52 | >10 | >10 | 7.82 | >10 |
| 4 | >10 | >10 | >10 | 5.56 | 8.04 | >10 |
| 11 | — | — | — | — | >10 | 0.3 |
| 14 | 2.0 | 0.4 | >10 | 2.0 | 0.8 | 3.0 |
| 5 | 5.04 | >10 | >10 | 1.57 | 2.56 | 4.45 |
| 12 | 4.0 | 2.0 | 10 | 2.0 | 1.0 | 2.0 |
| 13 | 1.0 | 1.0 | 7.0 | 0.8 | 0.3 | 1.0 |

As can be seen all of the compounds exhibited some anticancer activity. Of particular note compound 19 was more active than compound Y against 4 of the 6 cell lines tested, the 5' ProTide having the same phosphoramidate moiety as compound 19.

Example 2: Further In Vitro Cytotoxicity Studies

A subset of compounds of the invention were then assayed for their cytotoxic activity in a broader array of different solid tumours and haematological malignancies using the following assay.

Solid Tumour and Haematological Malignancy Assay

In vitro viability assay was performed to assess the effects of compounds on cell viability in selected cell lines over 72 h using the CellTiterGlo (CTG, Promega-G7573) assay. The tests were performed in duplicates with treatment of compounds at 9 points, 3.16 folds titration in 96 well plates over ~72 h. The compound starting concentrations were 198 mM. Cell viability assay using CellTiterGlo in 96-well plate were performed. Compounds were dissolved to 40 mM with thawed 100% DMSO. Compounds were serially diluted at 3.16-fold in thawed DMSO, and warmed to 37° C. before being dissolved in media (2 µl+200 µl). After compounds were dissolved in media, media containing compounds were warmed to 37° C. in incubator and then compounds in media were added to cell plates (50 µl+50 µl) in duplicates. The compounds' final concentrations were from 198 µM to 19.9 nM. Solubility of all compounds was checked and recorded again, then the plates were transferred to $CO_2$ tissue culture incubator immediately and incubated for 3 days. DMSO final concentration is 0.5%.

The results of the further screening are presented in Table 2.

TABLE 2

| Compound | HL-60 Promyelocytic leukaemia | | KG-1 Acute myelogenous leukaemia | | Z-138 Mantle cell lymphoma | | HEL92. 1.7 Erythroleukaemia | | RL Non-Hodgkin's lymphoma | | MCF-7 Mammary epithelial adenocarcinoma | |
| --- | --- | --- | --- | --- | --- | --- | --- | --- | --- | --- | --- | --- |
| | $EC_{50}$ (µM) Ab | Top Inhibition (%) | $EC_{50}$ (µM) Ab | Top Inhibition (%) | $EC_{50}$ (µM) Ab | Top Inhibition (%) | $EC_{50}$ (µM) Ab | Top Inhibition (%) | $EC_{50}$ (µM) Ab | Top Inhibition (%) | $EC_{50}$ (µM) Ab | Top Inhibition (%) |
| Cladribine | <0.019 | 85 | 0.17 | 93.5 | <0.019 | 99.7 | <0.019 | 97.4 | <0.019 | 94.7 | >198 | 36.3 |
| 6 | 0.23 | 96 | 1.2 | 98.6 | 1.5 | 101 | 0.07 | 98.6 | 0.29 | 98.6 | 6.8 | 102 |
| 7 | 0.27 | 98 | 1.5 | 98.8 | 1.07 | 101 | 0.07 | 98.6 | 0.5 | 100 | 5.45 | 103 |
| 8 | 0.46 | 96 | 2.75 | 98.4 | 3.5 | 100 | 0.18 | 98.3 | 0.85 | 98.1 | 7.97 | 101 |
| 9 | 0.13 | 87.7 | 0.8 | 96.9 | 0.051 | 99.9 | 0.044 | 97.2 | 0.14 | 89.9 | 21 | 100 |
| 10 | 0.12 | 87.7 | 0.6 | 95 | 0.047 | 100 | 0.042 | 97.2 | 0.15 | 89.8 | 22 | 99.2 |

Table 2 shows that the compounds of the invention are particularly effective in solid tumour as can be seen from the results for the MCF-7 cell line.

Example 3—Assessment of Cytotoxicity and Cancer Stem Cell Activity

A further comparative analysis of the toxicity of compounds in the KG1a cell line over an extended dose range was carried out, and the relative effect assessed of the compounds on the leukaemic stem cell compartment within the KG1a cell line, across the entire dose range. Thus, experimental tests were performed on certain compounds of the present invention to assess their ability to target cancer stem cells in a leukaemic cell line. The acute myeloid leukaemia (AML) cell line, KG1a, was employed to assess the relative effect of compounds on the stem cell compartment. The KG1a cell line was selected because it manifests a minor stem cell-like compartment with a distinct immunophenotype (Lin$^-$/CD34$^+$/CD38$^-$/CD123$^+$).

Materials and Methods
KG1a Cell Culture Conditions

Cells of the KG1a cell line were maintained in RPMI medium (Invitrogen, Paisley, UK) supplemented with 100 units/ml penicillin, 100 µg/ml streptomycin and 20% foetal calf serum. Cells were subsequently aliquoted (10$^5$ cells/100 µl) into 96-well plates and were incubated at 37° C. in a humidified 5% carbon dioxide atmosphere for 72 h in the presence of nucleoside analogues and their respective phosphoramidates at concentrations that were experimentally determined for each series of compounds. In addition, control cultures were carried out to which no drug was added. Cells were subsequently harvested by centrifugation and were analyzed by flow cytometry using the Annexin V assay.

Measurement of in vitro apoptosis. Cultured cells were harvested by centrifugation and then resuspended in 195 µl of calcium-rich buffer. Subsequently, 5 µl of Annexin V (Caltag Medsystems, Botolph Claydon, UK) was added to the cell suspension and cells were incubated in the dark for 10 mins prior to washing. Cells were finally resuspended in 190 µl of calcium-rich buffer together with 10 µl of propidium iodide. Apoptosis was assessed by dual-colour immunofluorescent flow cytometry as described previously. Subsequently LD$_{50}$ values (the dose required to kill 50% of the cells in a culture) were calculated for each nucleoside analogue and phosphoramidate.

Immunophenotypic Identification of the Leukaemic Stem Cell Compartment

KG1a cells were cultured for 72 h in the presence of a wide range of concentrations of each compound assayed. Cells were then harvested and labelled with a cocktail of anti-lineage antibodies (PE-cy7), anti-CD34 (FITC), anti-CD38 (PE) and anti-CD123 (PERCP cy5). The sub-population expressing a leukaemic stem cell (LSC) phenotype were subsequently identified and were expressed as a percentage of all viable cells left in the culture. The percentages of stem cells remaining were then plotted on a dose-response graph and the effects of the compounds were compared with 8-chloroadenosine.

Statistical Analysis

The data obtained in these experiments were evaluated using one way ANOVA. All data was confirmed as Gaussian or a Gaussian approximation using the omnibus K2 test. LD$_{50}$ values were calculated from the non-linear regression and line of best-fit analysis of the sigmoidal dose-response curves. All statistical analyses were performed using Graphpad Prism 6.0 software (Graphpad Software Inc., San Diego, Calif.).

Results

In Vitro Cytotoxicity

The in vitro drug sensitivity was measured using the Annexin V/propidium iodide assay. The LD$_{50}$ values calculated are also shown in Table 5.

TABLE 3

| Compound | LD$_{50}$ µm | Stem cell %<br>Control: 4% |
|---|---|---|
| Cladribine | 0.18 | 6 |
| 18 | 0.27 | 4 |
| 19 | 0.83 | 3.1 |
| Y | 1.7 | 2 |

Both compounds 18 and 19 exhibited stem cell selectivity. Compound 19 was more potent than compound Y, the 5'-ProTide having the same phosphoramidate moiety as compound 19. Compound 18 showed preferential targeting of LSCs when compared to cladribine.

Example 4: In Vitro Cytotoxicity Studies in Cells Infected with *Mycoplasma*

Tumor cell cultures were infected with *M. hyorhinis* (ATCC 17981) and after two or more passages (to avoid bias by the initial inoculum) successful infection was confirmed using the MycoAlert™ mycoplasma detection kit (Lonza, Basel, Switzerland). Although this assay is only semi-quantitative, a maximal infection was observed 3 to 4 days after subcultivation of the mycoplasma-exposed cells. Chronically infected tumor cell lines are further referred to as Cell line.Hyor. All tumor cell cultures were maintained in Dulbecco's modified Eagle's medium (DMEM) (Invitrogen) supplemented with 10% fetal bovine serum (Biochrom AG, Berlin, Germany), 10 mm HEPES, and 1 mm sodium pyruvate (Invitrogen). Cells were grown at 37° C. in a humidified incubator with a gas phase containing 5% CO$_2$.

The cytostatic activity of the test compounds was examined in mycoplasma-infected and uninfected cancer cell lines. When assaying the effect of *M. hyorhinis* infection, monolayer MCF7 and MCF7.Hyor cells were seeded in 48-well microtiter plates (Nunc™, Roskilde, Denmark) at 10,000 cells/well (Corning Inc., Corning, N.Y.) at 100,000 cells/well. After 24 h, the cells were exposed to different concentrations of test compound and allowed to proliferate for 72 h (to ensure sufficient cell proliferation and mycoplasma growth) after which the cells were trypsinized and counted using a Coulter counter (Analis, Suarlée, Belgium). Suspension cells (L1210, L1210.Hyor, FM3A, and FM3A.Hyor) were seeded in 96-well microtiter plates (Nunc) at 60,000 cells/well in the presence of different concentrations of test compound. The cells were allowed to proliferate for 48 h and then counted using a Coulter counter. The 50% inhibitory concentration (IC$_{50}$) was defined as the compound concentration required to reduce cell proliferation by 50%.

TABLE 4

| Compound | MCF7 μM | MCF7/HYOR μM | Loss of potency |
|---|---|---|---|
| Cladribine | 0.37 | 9.3 | 25-fold |
| 19 | 5.2 | 26 | 5-fold |
| Y | 2.1 | 33 | 16-fold |

Compound 19 showed a smaller loss of potency against MCF7 cells infected with *Mycoplasma hyorhinis* than both compound Y, the 5'-ProTide having the same phosphoramidate moiety as compound 19 and cladribine.

TABLE 5

| CPF | L1210 μM | L1210/HYOR μM | Loss of potency |
|---|---|---|---|
| Cladribine | 0.4 | 3.0 | 8-fold |
| 6 | 1.0 | 4 | 4-fold |

Compound 6 showed a smaller loss of potency against L1210 cells infected with *Mycoplasma hyorhinis* than cladribine.

The invention claimed is:

1. A compound of formula (I) or a pharmaceutically acceptable salt thereof:

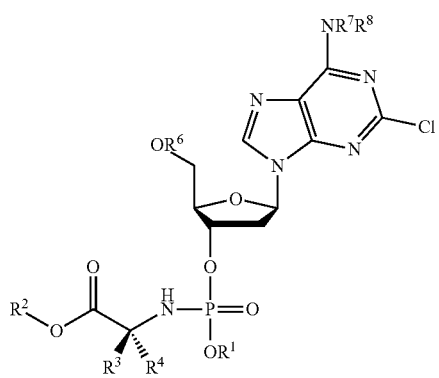

(I)

wherein:
$R^1$ is aryl;
$R^2$ is selected from the group consisting of $C_1$-$C_{24}$-alkyl, $C_3$-$C_{24}$-alkenyl, $C_3$-$C_{24}$-alkynyl, $C_0$-$C_4$-alkylene-$C_3$-$C_7$-cycloalkyl and $C_0$-$C_4$-alkylene-aryl;
$R^3$ and $R^4$ are each independently selected from the group consisting of H, $C_1$-$C_6$-alkyl and $C_1$-$C_3$-alkylene-$R^9$; or $R^3$ and $R^4$ together with the atom to which they are attached form a $C_3$-$C_6$-cycloalkyl or 3-6 membered heterocycloalkyl group, wherein said heterocycloalkyl group comprises at least one heteroatom selected from O, N, and S;
$R^5$ and $R^7$ are each independently selected from the group consisting of H and $C_1$-$C_4$-alkyl;
$R^6$ is independently selected from the group consisting of H and $C(O)R^{10}$;
$R^8$ is independently selected from the group consisting of H, $C(O)OR^{10}$ and $C(O)R^{10}$;

$R^9$ is independently selected from the group consisting of aryl, imidazolyl, indolyl, $SR^a$, $OR^a$, $CO_2R^a$, $CO_2NR^aR^a$, $NR^aR^b$ and $NH(=NH)NH_2$;
$R^{10}$ is independently at each occurrence selected from the group consisting of $C_1$-$C_{24}$-alkyl, $C_3$-$C_{24}$-alkenyl, $C_3$-$C_{24}$-alkynyl, $C_0$-$C_4$-alkylene-$C_3$-$C_7$-cycloalkyl and $C_0$-$C_4$-alkylene-aryl;
wherein any aryl group is selected from the group consisting of phenyl, naphthyl and tetrahydronaphthyl; and
wherein any phenyl, alkyl, alkynyl, alkenyl, alkylene, cycloalkyl, naphthyl or tetrahydronaphthyl group is optionally substituted with from 1 to 4 substituents selected from the group consisting of halo, nitro, cyano, $NR^aR^a$, $NR^aS(O)_2R^a$, $NR^aC(O)R^a$, $NR^aCONR^aR^a$, $NR^aCO_2R^a$, $OR^a$, $SR^a$, $SOR^a$, $SO_3R^a$, $SO_2R^a$, $SO_2NR^aR^a$, $CO_2R^a$ $C(O)R^a$, $CONR^aR^a$, $CR^aR^a$ $NR^aR^a$, $C_1$-$C_4$-alkyl, $C_2$-$C_4$-alkenyl, $C_2$-$C_4$-alkynyl and $C_1$-$C_4$-haloalkyl; and
wherein $R^a$ is independently at each occurrence selected from the group consisting of H and $C_1$-$C_4$-alkyl; and $R^b$ is independently at each occurrence selected from the group consisting of H, $C_1$-$C_4$-alkyl, $C(O)$—$C_1$-$C_4$-alkyl, and $S(O)_2$—$C_1$-$C_4$-alkyl.

2. The compound of claim 1, wherein the compound is represented by formula (II):

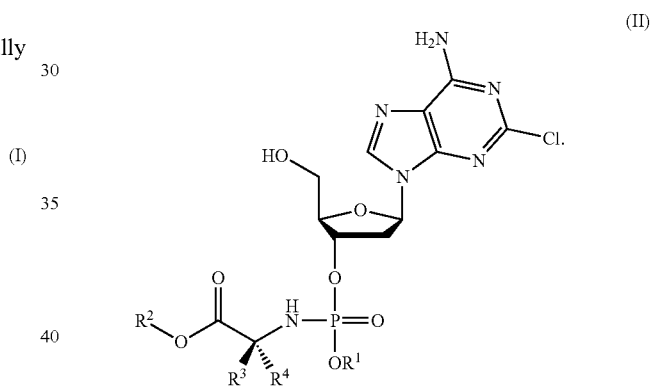

(II)

3. The compound of claim 1, wherein $R^1$ is substituted or unsubstituted phenyl.
4. The compound of claim 3, wherein $R^1$ is unsubstituted phenyl.
5. The compound of claim 1, wherein $R^1$ is 1-naphthyl.
6. The compound of claim 1, wherein $R^2$ is $C_4$-$C_8$-alkyl.
7. The compound of claim 6, wherein $R^2$ is selected from the group consisting of iso-butyl, tert-butyl, n-butyl, n-pentyl, $CH_2C(Me)_3$ and n-hexyl.
8. The compound of claim 1, wherein $R^2$ is $C_5$-$C_7$-cycloalkyl.
9. The compound of claim 8, wherein $R^2$ is unsubstituted cyclohexyl.
10. The compound of claim 1, wherein $R^2$ is $CHR^{11}$-phenyl; wherein $R_{11}$ is selected from the group consisting of H and $C_1$-$C_4$-alkyl.
11. The compound of claim 10, wherein $R^2$ is unsubstituted benzyl.
12. The compound of claim 1, wherein one of $R^3$ and $R^4$ is H and the other is selected from the group consisting of H, Me, isopropyl, isobutyl and benzyl.
13. The compound of claim 12, wherein $R^4$ is H; and $R^3$ is selected from the group consisting of H, Me, isopropyl, isobutyl and benzyl.

14. The compound of claim 13, wherein R$^4$ is H; and R$^3$ is Me.
15. The compound of claim 1, wherein the compound is selected from the group consisting of:
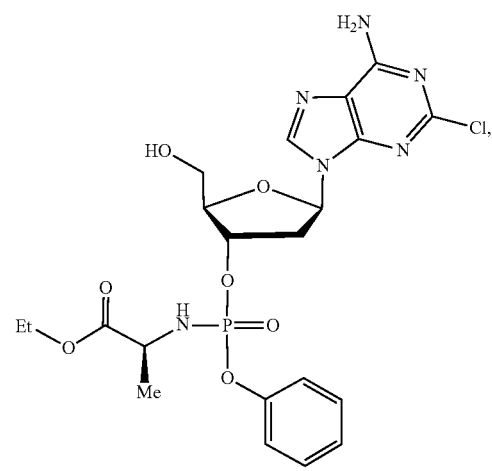
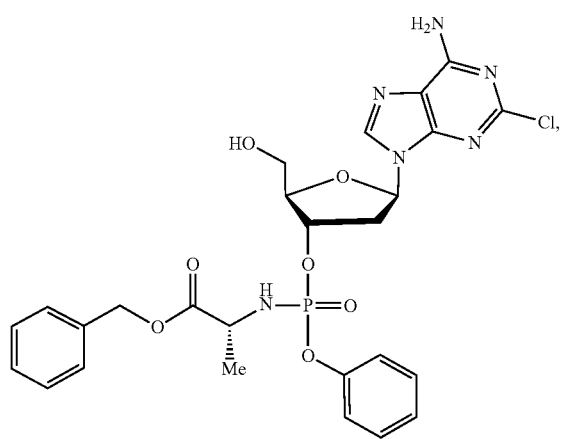 [SMILES: C[C@H](NP(=O)(Oc1ccccc1)O[C@@H]1C[C@H](n2cnc3c(N)nc(Cl)nc32)O[C@@H]1CO)C(=O)OCc1ccccc1]
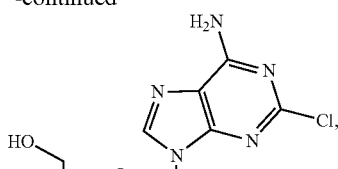
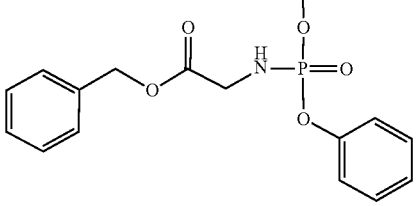
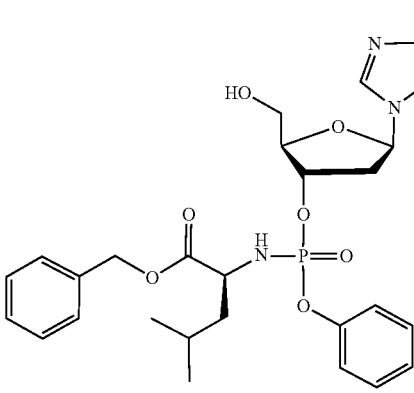
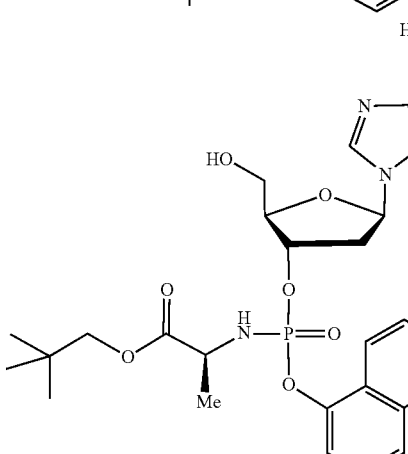
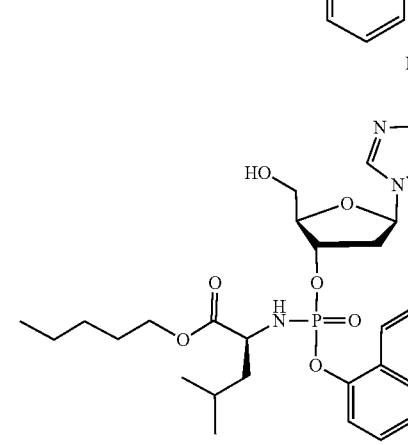

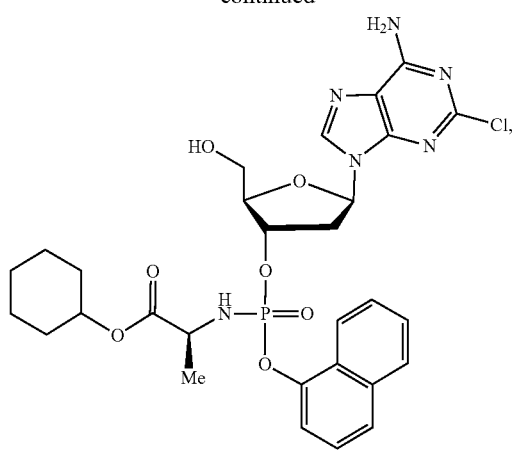
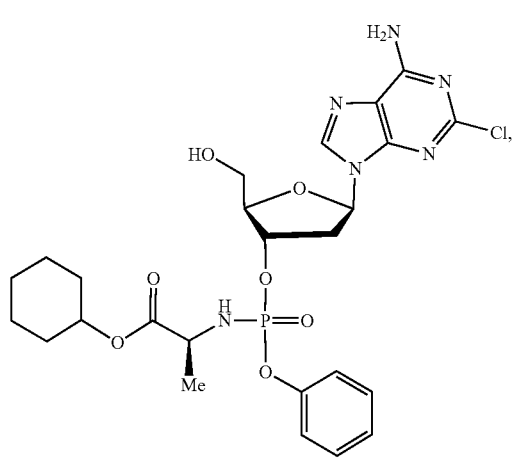
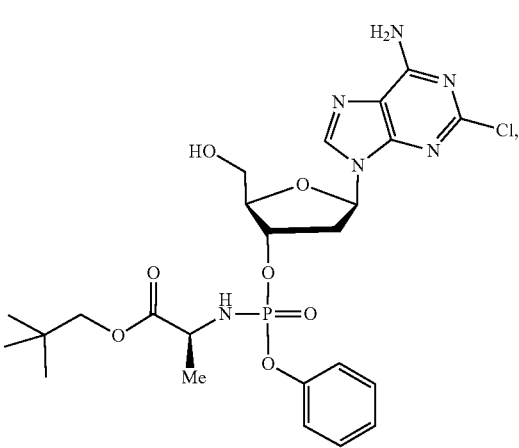
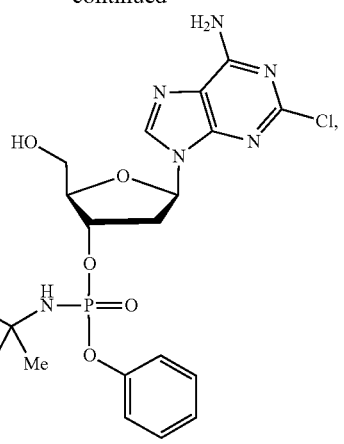
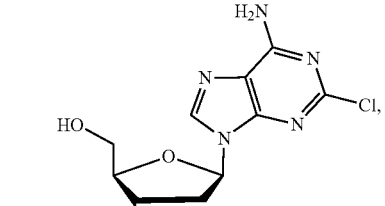
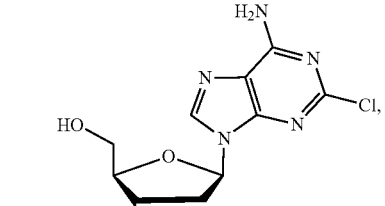

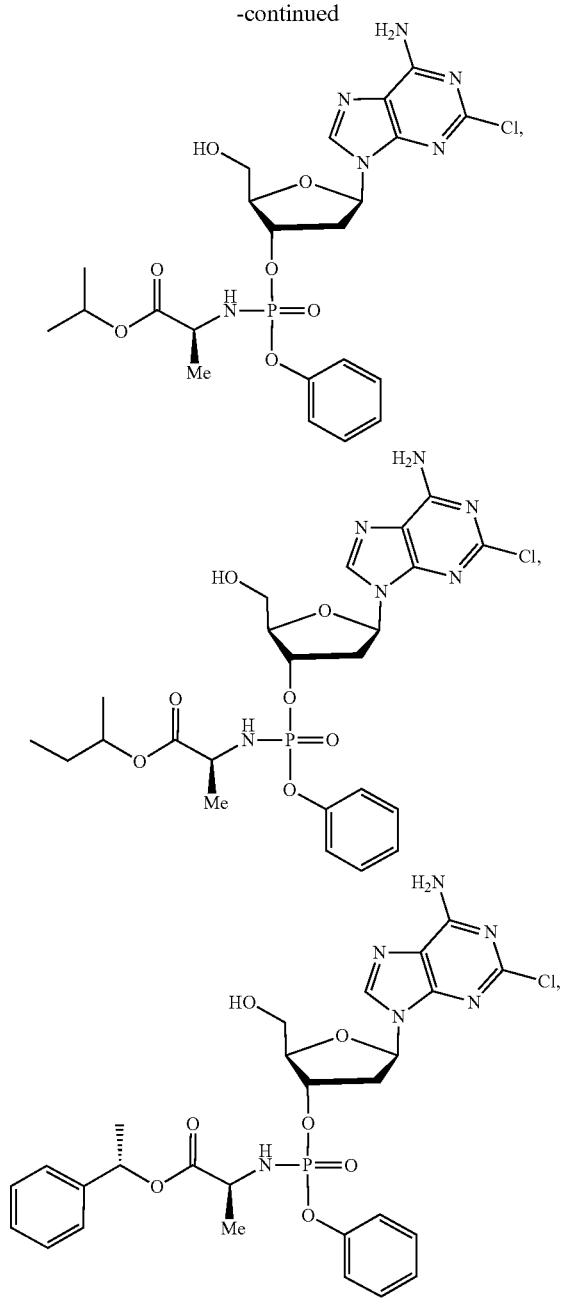
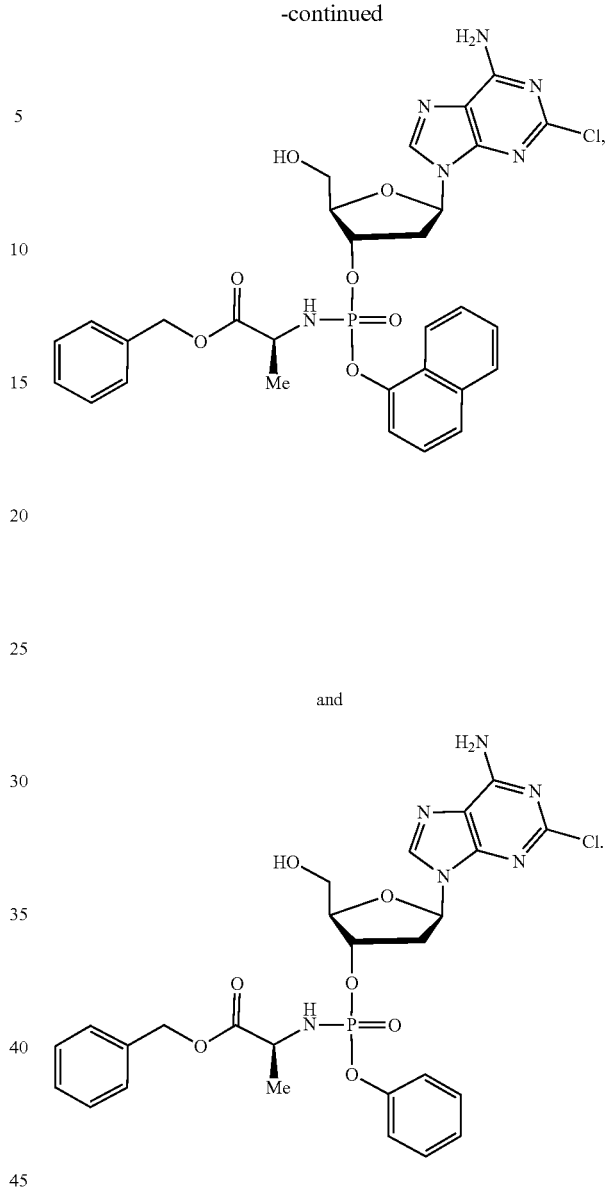
16. A pharmaceutical composition comprising a compound of claim 1 in combination with a pharmaceutically acceptable excipient.